US009999658B2

(12) United States Patent
Wen et al.

(10) Patent No.: US 9,999,658 B2
(45) Date of Patent: Jun. 19, 2018

(54) METHOD FOR TREATING PAIN AND METHOD FOR SCREENING PHARMACEUTICAL COMPOSITIONS HAVING AN ANTI-PAIN EFFECT

(71) Applicant: National Sun Yat-sen University, Kaohsiung (TW)

(72) Inventors: Zhi-Hong Wen, Kaohsiung (TW); Ming-Hong Tai, Kaohsiung (TW); Shi-Ying Huang, Kaohsiung (TW); Chun-Sung Sung, Taipei (TW); Wu-Fu Chen, Kaohsiung (TW); Chun-Hong Chen, Kaohsiung (TW); Chien-Wei Feng, Kaohsiung (TW); Han-Chun Hung, Kaohsiung (TW); Hui-Min David Wang, Kaohsiung (TW); Nan-Fu Chen, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 0 days. days.

(21) Appl. No.: 15/073,660

(22) Filed: Mar. 18, 2016

(65) Prior Publication Data
US 2017/0087222 A1 Mar. 30, 2017

(30) Foreign Application Priority Data
Sep. 25, 2015 (TW) .............................. 104131766 A

(51) Int. Cl.
*A61K 38/46* (2006.01)
*G01N 33/50* (2006.01)
*A61K 31/7088* (2006.01)
*A61K 48/00* (2006.01)
*C12N 15/00* (2006.01)

(52) U.S. Cl.
CPC ........ *A61K 38/465* (2013.01); *A61K 31/7088* (2013.01); *A61K 48/00* (2013.01); *C12N 15/00* (2013.01); *G01N 33/5088* (2013.01); *C12Y 301/03016* (2013.01); *G01N 2333/916* (2013.01)

(58) Field of Classification Search
None
See application file for complete search history.

(56) References Cited

PUBLICATIONS

Kay, Nature Reviews Genetics, advance online publication, pp. 1-13, published online Apr. 6, 2011.*
Misra, JAPI, 61: 127-133, 2013.*

* cited by examiner

*Primary Examiner* — Antonio Galisteo Gonzalez
(74) *Attorney, Agent, or Firm* — Hannah M. Tien

(57) ABSTRACT

The present invention relates to a method for treating pain in a subject in need thereof, comprising administering an effective amount of a nucleic acid to the subject, wherein the nucleic acid comprises a PTEN nucleotide sequence of SEQ ID NO: 1. The present invention also provides a method for screening pharmaceutical compositions having an anti-pain effect, wherein the pharmaceutical compositions can stimulate the upregulation of PTEN.

7 Claims, 14 Drawing Sheets
(6 of 14 Drawing Sheet(s) Filed in Color)

(A)

(B)

(C)

SEQUENCE LISTING

<160> NUMBER OF SEQ ID NOS: 1

<210> SEQ ID NO 1
<211> LENGTH: 403
<212> TYPE: PRT
<213> ORGANISM: Human adenovirus type 1

<400> SEQUENCE: 1

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30
```

-continued

```
Ile Ala Met Gly Phe Pro Ala Glu Arg Leu Glu Gly Val Tyr Arg Asn
         35                  40                  45
Asn Ile Asp Asp Val Val Arg Phe Leu Asp Ser Lys His Lys Asn His
     50                  55                  60
Tyr Lys Ile Tyr Asn Leu Cys Ala Glu Arg His Tyr Asp Thr Ala Lys
 65                  70                  75                  80
Phe Asn Cys Arg Val Ala Gln Tyr Pro Phe Glu Asp His Asn Pro Pro
                 85                  90                  95
Gln Leu Glu Leu Ile Lys Pro Phe Cys Glu Asp Leu Asp Gln Trp Leu
                100                 105                 110
Ser Glu Asp Asp Asn His Val Ala Ala Ile His Cys Lys Ala Gly Lys
                115                 120                 125
Gly Arg Thr Gly Val Met Ile Cys Ala Tyr Leu Leu His Arg Gly Lys
            130                 135                 140
Phe Leu Lys Ala Gln Glu Ala Leu Asp Phe Tyr Gly Glu Val Arg Thr
145                 150                 155                 160
Arg Asp Lys Lys Gly Val Thr Ile Pro Ser Gln Arg Arg Tyr Val Tyr
                165                 170                 175
Tyr Tyr Ser Tyr Leu Leu Lys Asn His Leu Asp Tyr Arg Pro Val Ala
                180                 185                 190
Leu Leu Phe His Lys Met Met Phe Glu Thr Ile Pro Met Phe Ser Gly
                195                 200                 205
Gly Thr Cys Asn Pro Gln Phe Val Val Cys Gln Leu Lys Val Lys Ile
            210                 215                 220
Tyr Ser Ser Asn Ser Gly Pro Thr Arg Arg Glu Asp Lys Phe Met Tyr
225                 230                 235                 240
Phe Glu Phe Pro Gln Pro Leu Pro Val Cys Gly Asp Ile Lys Val Glu
                245                 250                 255
Phe Phe His Lys Gln Asn Lys Met Leu Lys Lys Asp Lys Met Phe His
                260                 265                 270
Phe Trp Val Asn Thr Phe Phe Ile Pro Gly Pro Glu Glu Thr Ser Glu
            275                 280                 285
Lys Val Glu Asn Gly Ser Leu Cys Asp Gln Glu Ile Asp Ser Ile Cys
            290                 295                 300
Ser Ile Glu Arg Ala Asp Asn Asp Lys Glu Tyr Leu Val Leu Thr Leu
305                 310                 315                 320
Thr Lys Asn Asp Leu Asp Lys Ala Asn Lys Asp Lys Ala Asn Arg Tyr
                325                 330                 335
Phe Ser Pro Asn Phe Lys Val Lys Leu Tyr Phe Thr Lys Thr Val Glu
            340                 345                 350
Glu Pro Ser Asn Pro Glu Ala Ser Ser Ser Thr Ser Val Thr Pro Asp
            355                 360                 365
Val Ser Asp Asn Glu Pro Asp His Tyr Arg Tyr Ser Asp Thr Thr Asp
        370                 375                 380
Ser Asp Pro Glu Asn Glu Pro Phe Asp Glu Asp Gln His Thr Gln Ile
385                 390                 395                 400
Thr Lys Val
```

METHOD FOR TREATING PAIN AND METHOD FOR SCREENING PHARMACEUTICAL COMPOSITIONS HAVING AN ANTI-PAIN EFFECT

CROSS-REFERENCES TO RELATED APPLICATIONS

The present application claims priority to Taiwan Patent Application No. 104131766, incorporated herein by reference in its entirety. The sequence listing text file, file name 2472-NCSU-US_PTENseq_ST25, file size 3786 bytes, is incorporated herein by reference in its entirety.

FIELD OF THE INVENTION

The present invention relates to a method for treating pain by upregulating phosphatase and tensin homolog deleted from chromosome 10 (hereinafter "PTEN") to inhibit or to alleviate neuropathic pain.

BACKGROUND OF THE INVENTION

Pain affects 1.5 billion people globally, including 116 million people in the USA and 164 million people in Europe and Israel combined. The 2009 global pain market was estimated to be over US $50 billion. Previous studies indicated that chronic pain occurs in about 20% of the general population, and the prevalence of neuropathic pain is 6.9%.

The clinical syndromes of the patients with neuropathic pain are accompanied by hyperalgesia, allodynia and spontaneous pain. In the same time, the use of opioids and other analgesics (including the non-steroidal anti-inflammatory drugs) will cause analgesic tolerance. In a review of 174 trials published, Finnerup et al. reported that there are no drug treatments available that can relieve all neuropathic pain conditions. (Finnerup N B et al., *Pain.* 150:573-81 (2010)) Moreover, the detailed mechanisms underlying neuropathic pain remain unclear. Therefore, the recent pain researches still focus on clarifying the possible mechanisms.

Clinical neuropathic pain syndromes are characterized by nociceptive behaviors such as evoked pain (hyperalgesia, mechanical allodynia and cold allodynia) and spontaneous pain (weight-bearing deficits) (Baron R., *Handb Exp Pharmacol.* 194:3-30. doi:10.1007/978-3-540-79090-7_1 (2009)), which can be measured by the nociceptive behavioral testing.

Spinal neuroinflammation may accelerate central sensitization and promote the development and maintenance of neuropathic pain, and spinal neuroinflammation is characterized by microglial and astrocytic activation and increased expression of the pro-inflammatory mediator tumor necrosis factor-α (hereinafter "TNF-α"). (Lin Y C et al., *Behav Pharmacol.*, 22:739-50 (2011); Chen N F et al., *J Pain.*, 14:1671-85 (2013))

Central sensitization within the dorsal horn of the spinal cord could contribute to the hypersensitive pain behaviors commonly observed with neuropathic pain. Activation of microglia and astrocytes could accelerate central sensitization. (Costigan M et al., *Annu Rev Neurosci.* 32:1-32 (2009); Myers R R et al., *Drug Discov Today.* 11:8-20 (2006); Streit W J et al., *J Neuroinflammation.* 2004; 1:14.) The nociceptive behaviors are accompanied by spinal microglial and astrocytic activation (Lin Y C et al., *Behav Pharmacol.* 22:739-50 (2011); Chen N F et al., *Mar Drugs.* 12:3792-817 (2014); Chen W F et al., *Biomaterials.* 53:1-11 (2015)), wherein the astrocyte plays an important role in nociceptive hypersensitization. (Fraser M M et al., *Cancer Res.* 64:7773-9 (2004); Ferraguti F et al., *Exp Brain Res.* 137:1-11 (2001))

Microglia and astrocytes play important roles for the maintenance as well as the development of neuropathic pain. (Hains B C and Waxman S G, *J Neurosci.* 26: 4308-17 (2006); Ji R R and Suter M R, *Mol Pain.* 3:33 (2007); Cao L et al., *Eur J Immunol.* 39:3562-9. (2009); Garrison C J et al., *Brain Res.* 565:1-7 (1991); Colburn R W et al., *J Neuroimmunol.* 79:163-75 (1997); Colburn R W et al., *Exp Neurol.* 157: 289-304 (1999); Coyle D E, *Glia.* 23:75-83 (1998); Stuesse S L et al., *Exp Brain Res.* 137:219-27 (2001))

Spinal microglia-astrocyte interactions could promote nociceptive responses. (Raghavendra V et al., *J Neurosci.* 20:467-73 (2004); Watkins L R et al., *Pain.* 71:225-35. (1997); Sung C S et al., *Glia.* 60:2004-17 (2012); Miyoshi K et al., *J Neurosci.* 28:12775-87 (2008); Davalos D et al., *Nat Neurosci.* 8:752-8 (2005); Lindia J A et al., *J Pain.* 6:434-8 (2005))

Upregulation of OX-42 (microglial marker) and GFAP (astrocytic marker) immunoreactivity in the spinal dorsal horn are known indicators of elevated nociceptive states. (Jean Y H et al., *Br J Pharmacol.* 158:713-25 (2009); Sweitzer S M et al., *J Pharmacol Exp Ther.* 297:1210-7 (2001); Ledeboer A et al., *Pain.* 115:71-83 (2005); Garrison C J et al., *Brain Res.* 565:1-7 (1991); Colburn R W et al., *J Neuroimmunol.* 79:163-75 (1997); Colburn R W et al., *Exp Neurol.* 157: 289-304 (1999); Coyle D E, *Glia.* 23:75-83 (1998); Stuesse S L et al., *Neurosci Lett.* 287: 121-4 (2000); Stuesse S L et al., *Exp Brain Res.* 137:219-27 (2001).)

Inhibition of microglial and astrocytic activation exerts analgesic effects. (Lin Y C et al., *Behav Pharmacol.* 22:739-50 (2011); Jean Y H et al., *Br J Pharmacol.* 158:713-25 (2009); Sweitzer S M et al., *J Pharmacol Exp Ther* 297: 1210-7 (2001); Ledeboer A et al., *Pain.* 115:71-83 (2005))

TNF-α plays key roles in neuropathic pain, whereas, inhibition of spinal TNF-α inhibits neuropathic pain behavior (Leung L and Cahill C M, *J Neuroinflammation.* 7:27 (2010); Youn D H et al., *J Neurosci Res.* 86: 2867-75 (2008); Milligan E D et al., *J Neurosci.* 23:1026-40 (2003)).

Intra-articular adenovirus-mediated PTEN (hereinafter "Ad-PTEN") has systemic anti-inflammatory effects. (Wang C R et al., *Arthritis Rheum.* 58:1650-6 (2008))

Inhibition of the spinal mammalian target of rapamycin (hereinafter "mTOR") pathway of neuropathic rats can attenuate nociception and reduce neuroinflammation, and PTEN is considered an upstream inhibitory mediator of mTOR. Therefore, PTEN pathway is probably used for inhibiting downstream signaling of mTOR (Adkins J R et al., *Am Surg.* 70:384-7. discussion 387-388. (2004); Dello Russo C et al., *Biochem Pharmacol.* 78:1242-51 (2009); Lisi L et al, *J Neuroinflammation.* 8:1 (2011); Dello Russo et al. *Glia.* 61:301-11 (2013); Zhang W et al., *Pharmacol Biochem Behav.* 111:64-70 (2013); Geranton S M et al., *J Neurosci.* 29: 15017-27 (2009); Asante C O et al., *J Pain.* 11:1356-67 (2010)).

PTEN is a tumor suppressor gene. PTEN has been studied extensively through cancer research. Previous study has demonstrated that targeted disruption of Pten in Schwann cells causes focal hypermyelination in the PNS and is associated with progressive peripheral neuropathy in mice (Goebbels S et al., *EMBO Mol Med.* 4:486-99 (2012)). However, there is still a lack of evidence to show the role that PTEN plays for modulating pain.

Previous neuroscience studies have focused on the role of PTEN in axon regeneration, Alzheimer's disease, Parkinson's disease, ischemic brain injury, and spinal cord injury. There have been no past studies to explore the therapeutic effects of upregulation of PTEN on pain.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
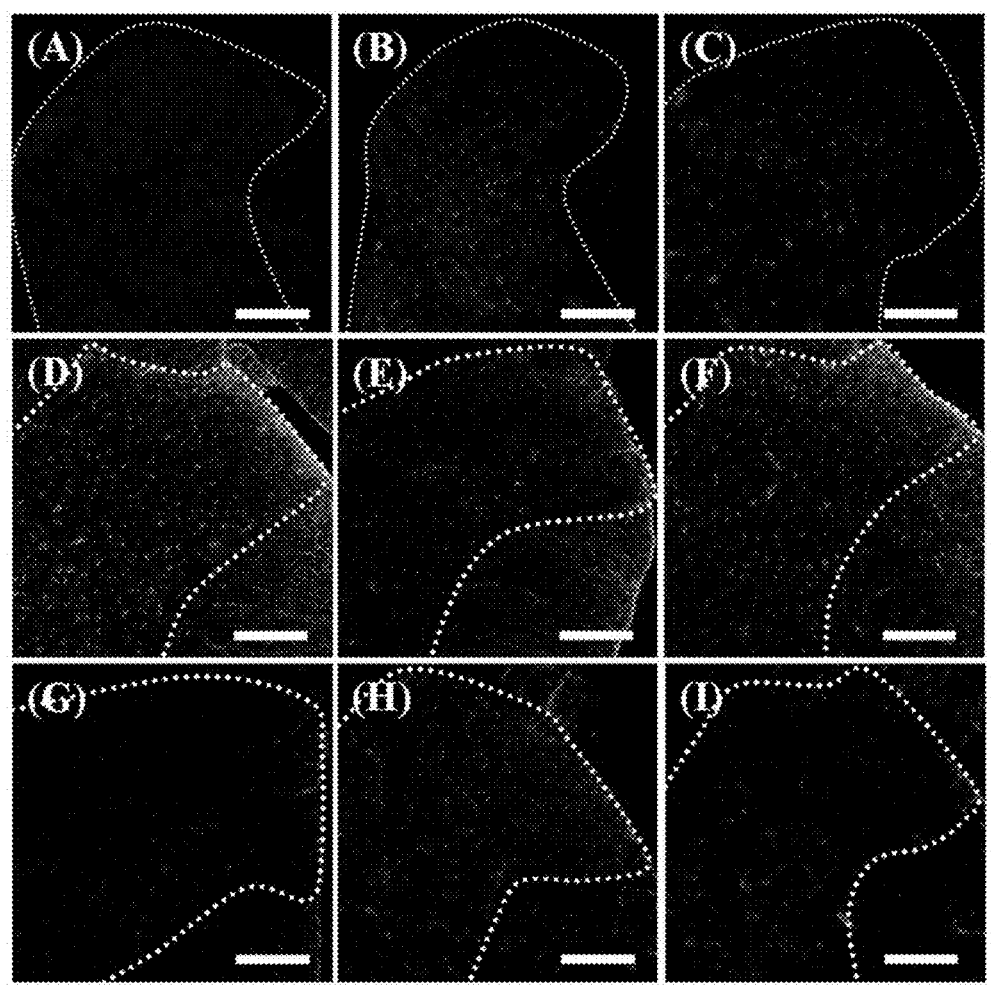
FIG. 1 shows the time course effects of CCI on spinal of rats, wherein (A) is the immunostaining image of phospho-PTEN from the sham-operated group; (B) is the immunostaining image of phospho-PTEN from the 7 days after CCI group; (C) is the immunostaining image of phospho-PTEN from the 14 days after CCI group; (D) is the immunostaining image of PTEN from the sham-operated group; (E) is the immunostaining image of PTEN from the 7 days after CCI group; (F) is the immunostaining image of PTEN from the 14 days after CCI group; (G) is the immunostaining image of phospho-mTOR from the sham-operated group; (H) is the immunostaining image of phospho-mTOR from the 7 days after CCI group; (I) is the immunostaining image of phospho-mTOR from the 14 days after CCI group; (J)-(L) are bar graphs of quantification of phospho-PTEN (J), PTEN (K), and phospho-mTOR (L) immunoreactivity from 1, 3, 7, and 14 days after CCI group as compared with the sham-operated group of rats; *$P<0.05$ compared with the sham-operated group. Scale bars: 200 µm for all images.
Figure 1:
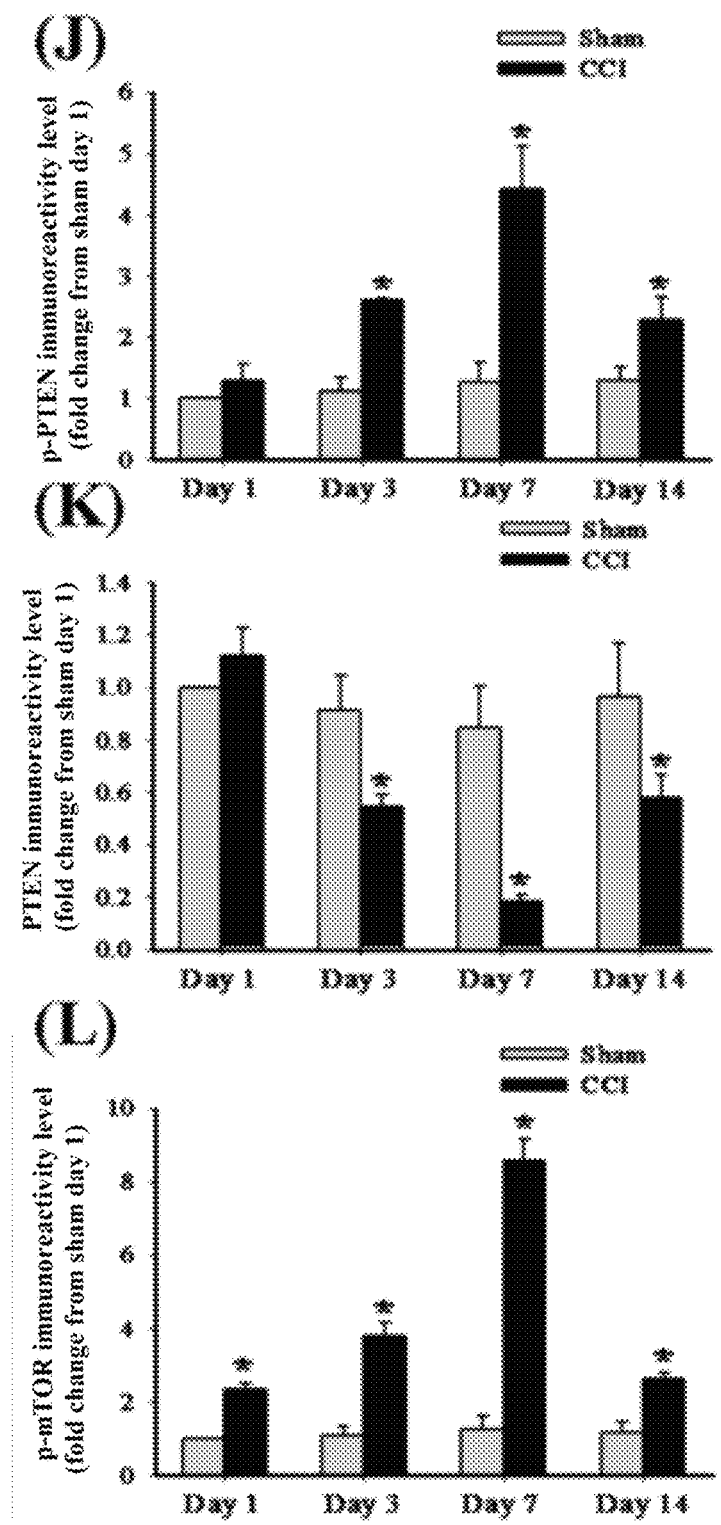

The present invention relates to a method for treating pain in a subject in need thereof, comprising administering an effective amount of a nucleic acid to the subject, wherein the nucleic acid comprises a PTEN nucleotide sequence of SEQ ID NO: 1. The present invention also provides a method for screening pharmaceutical compositions having an anti-pain effect, wherein the pharmaceutical compositions can stimulate the upregulation of PTEN.

DETAILED DESCRIPTION OF THE INVENTION

To the best of our knowledge, our report is the first to explore the role of PTEN for improving or treating pain, especially neuropathic pain. (The essay published in Journal of Neuroinflammation, published on 26 Mar. 2015, article name: "Involvement of phosphatase and tensin homolog deleted from chromosome 10 in rodent model of neuropathic pain" is incorporated herein by reference in its entirety.)

The terms and their abbreviations and acronyms used in the present invention are listed below:

| term | acronyms |
|---|---|
| adenovirus-mediated green fluorescent protein | Ad-GFP |
| adenovirus-mediated phosphatase and tensin homolog deleted from chromosome 10 | Ad-PTEN |
| adenovirus-mediated PTEN antisense oligonucleotide | Ad-antisense PTEN |
| chronic constriction injury | CCI |
| glial fibrillary acidic protein | GFAP |
| intrathecal | i.t. |
| mammalian target of rapamycin | mTOR |
| Neuronal Nuclei | NeuN |
| phosphorylated mammalian target of rapamycin | p-mTOR |
| phosphatase and tensin homolog deleted from chromosome 10 | PTEN |
| phosphorylated PTEN | p-PTEN |
| tumor necrosis factor-α | TNF-α |
| paw withdrawal latency | PWL |
| paw withdrawal threshold | PWT |

The present invention provides a method for treating pain in a subject, comprising administering an effective amount of nucleic acid to the subject, wherein the nucleic acid comprises, but not limited to, a PTEN nucleotide sequence SEQ ID NO: 1.

In one embodiment, Ad-PTEN is used for upregulating PTEN to treat pain, wherein the adenovirus vectors are delivered by an intrathecal (hereinafter "i.t.") delivery system.

In one embodiment, the pain is an acute pain or a chronic pain.

In one embodiment, the acute pain comprises central nervous system pain and peripheral nervous system pain, visceral pain, headache, migraine headache, Fothergill's neuralgia, atypical facial pain, arthralgia, bone pain, pain caused by cancers or tumor invasion, neuralgia caused by neuropathic pain syndromes, neuropathic pain or pain linked to neuroinflammation.

In one embodiment, the chronic pain comprises central nervous system pain and peripheral nervous system pain, visceral pain, headache, migraine headache, Fothergill's neuralgia, atypical facial pain, arthralgia, bone pain, pain caused by cancers or tumor invasion, neuralgia caused by neuropathic pain syndromes, neuropathic pain or pain linked to neuroinflammation.

In one embodiment, treating pain is to inhibit or to alleviate pain.

In one embodiment, compared with a sham-operated group of rats, the chronic constriction injury (hereinafter "CCI") group of rats show PTEN downregulation as well as phospho-PTEN and phospho-mTOR upregulation (FIG. 1 and FIG. 2 (A)-(C)), which shows t CCI will downregulate PTEN.

Figure 2:
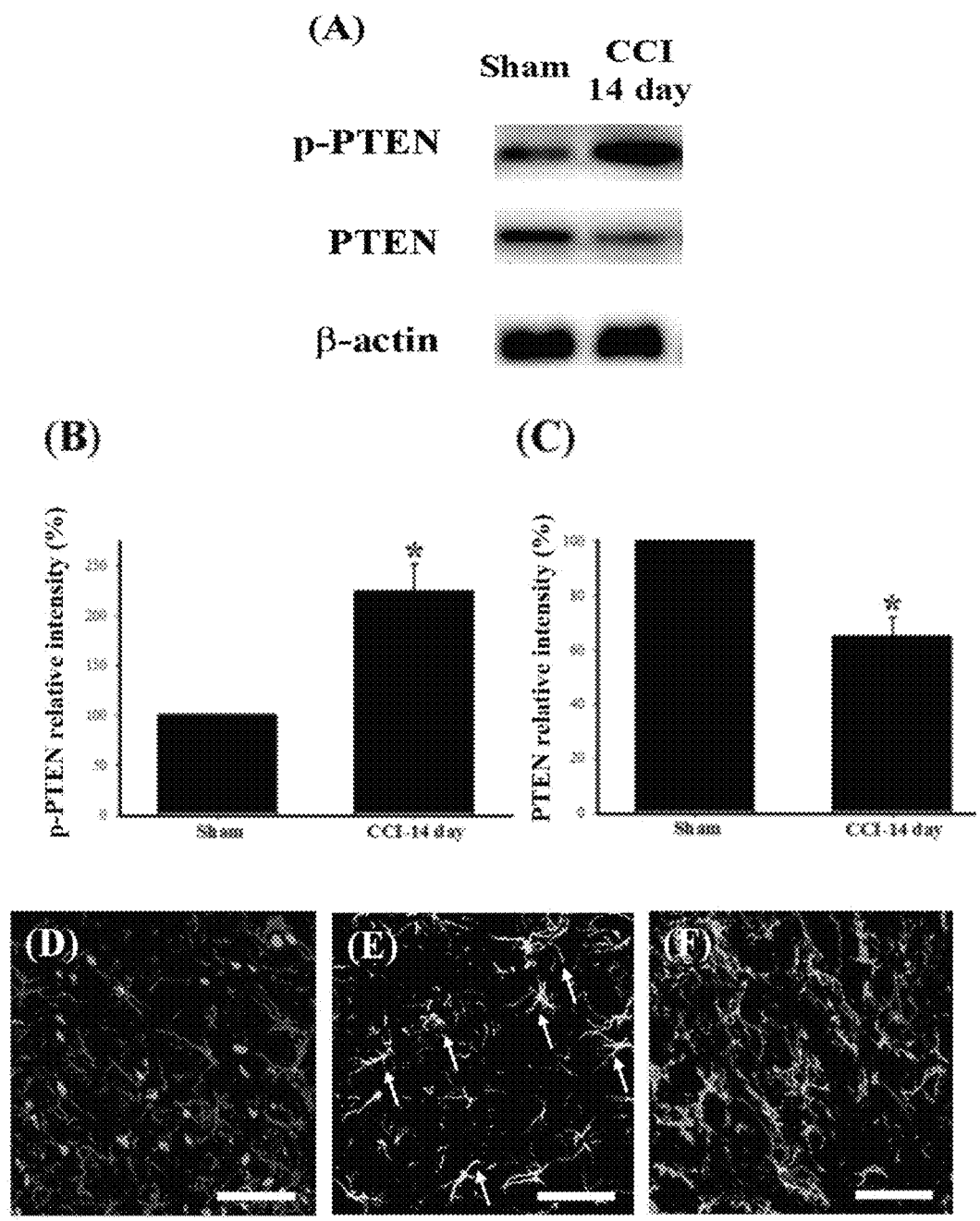
FIG. 2 shows the cellular specificity of endogenous PTEN in the dorsal horn of the spinal cord, wherein (A) shows Western blots for phospho-PTEN, PTEN, and β-actin proteins from sham-operated group of rats and 14 days after CCI group of rats; (B) shows relative density of immunoblot of phospho-PTEN; (C) shows relative density of immunoblot of PTEN; *$P<0.05$ compared with sham-operated group. (D)-(F) are respectively confocal double-immunofluorescent staining images of PTEN with NeuN (D), GFAP (E) and OX-42 (F). Scale bars are 50 µm for all images.

In one embodiment of a sham-operated group of rats, most PTEN signals are more often co-localized with astrocytes than with neuronal cells or microglial cells (FIG. 2 (D)-(F)).

Figure 3:
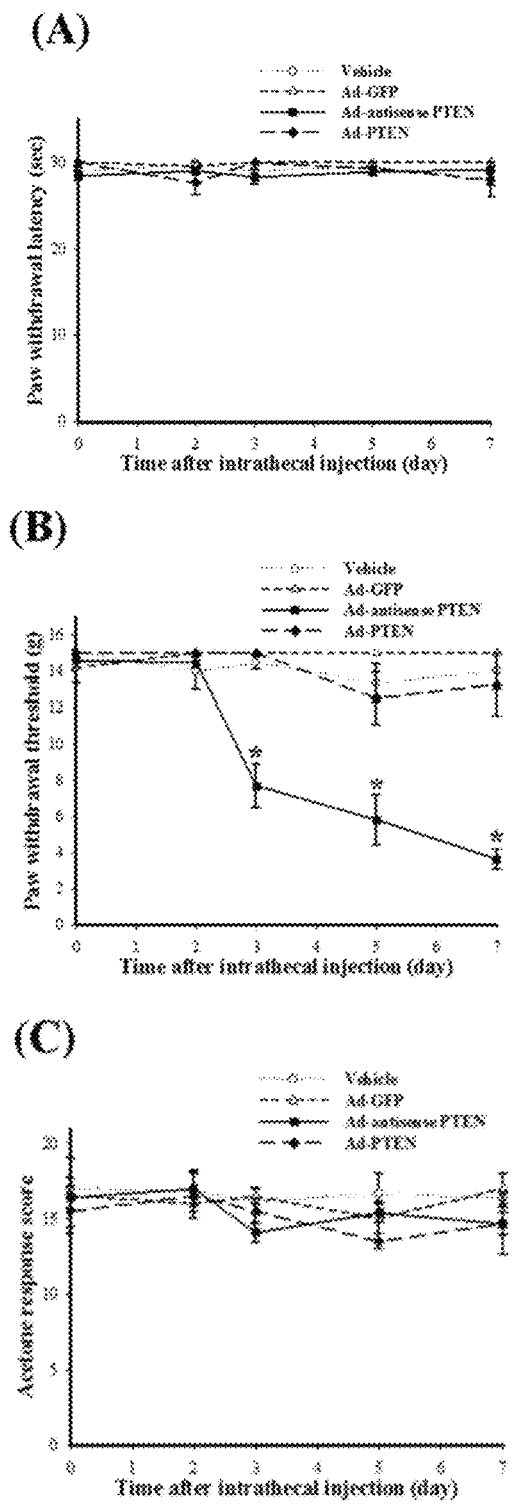
FIG. 3 shows time course of the effects of i.t. Ad-antisense PTEN on nociceptive behaviors in naïve group of rats, wherein (A) is the paw withdrawal latency (PWL); (B) is the paw withdrawal threshold (PWT); (C) is the acetone response scores of the paw; *$P<0.05$ compared with vehicle group.

In one embodiment, after i.t. injection of Ad-antisense PTEN, the naïve group of rats exhibit mechanical allodynia, which shows the downregulation of spinal PTEN is related with pain and can be used for treating pain (FIG. 3).

In another embodiment, compared with naïve plus i.t. vehicle group of rats and naïve plus i.t. Ad-GFP group of rats, the naïve plus i.t. Ad-PTEN group of rats, after i.t. injection of Ad-PTEN, shows significantly upregulated spinal PTEN immunoreactivity (FIG. 4 (D)). This result shows that the injection (i.t.) of Ad-PTEN causes the upregulation of PTEN, and the PTEN is primarily co-localized with astrocytes (FIG. 4 (E)-(G)).

Figure 5:
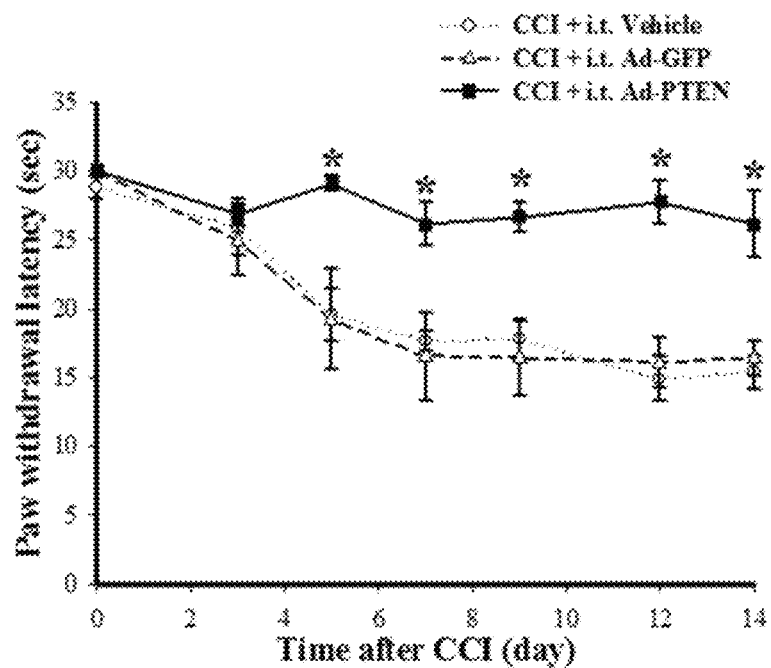
FIG. 5 shows the time course of i.t. Ad-PTEN effects on nociceptive behaviors in CCI group of rats, wherein (A) is thermal hyperalgesia; (B) is mechanical allodynia; (C) is cold allodynia; and (D) is weight-bearing deficits; *$P<0.05$ compared with CCI plus i.t. vehicle group.
Figure 5:
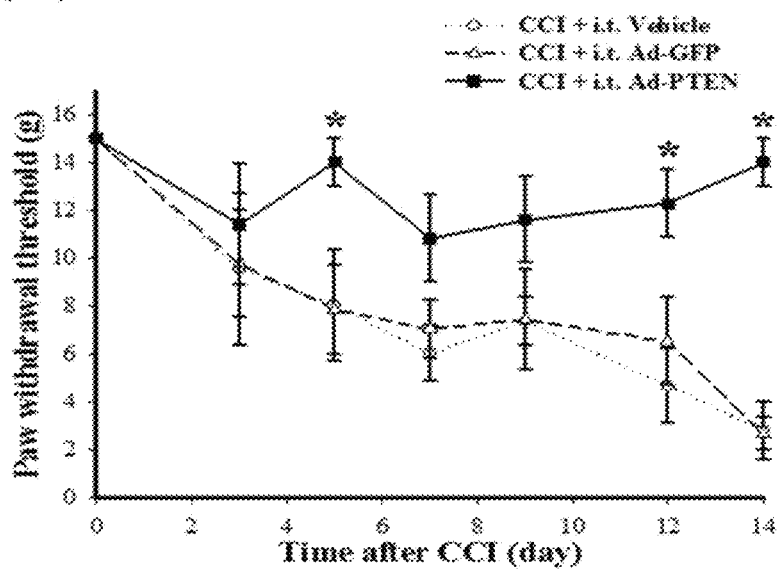
Figure 5:
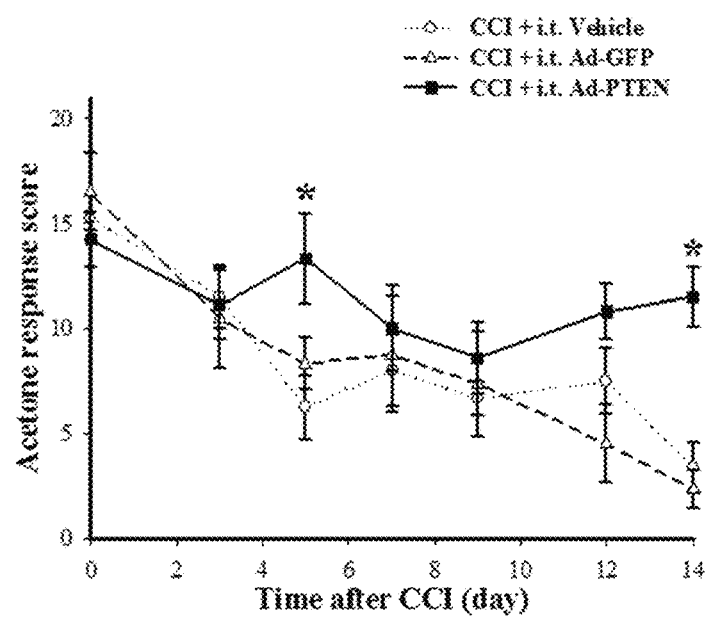
Figure 5:
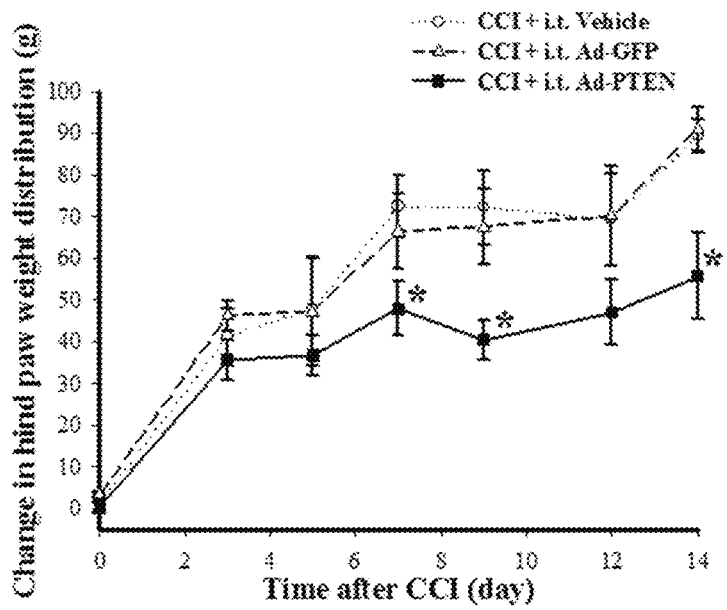
Figure 6:
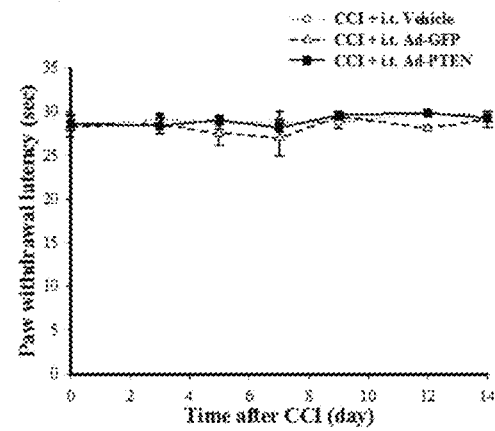
FIG. 6 shows time course of the effects of i.t. Ad-PTEN on nociceptive behaviors with the normal hindpaw (contralateral side of the injured hindpaw) in CCI group of rats, wherein (A) is thermal hyperalgesia test; (B) is mechanical allodynia test; and (C) is cold allodynia test.
Figure 6:
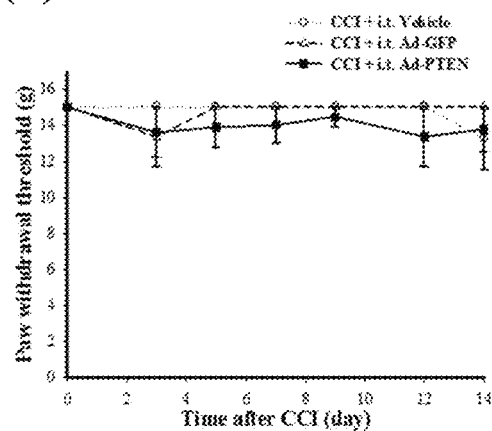
Figure 6:
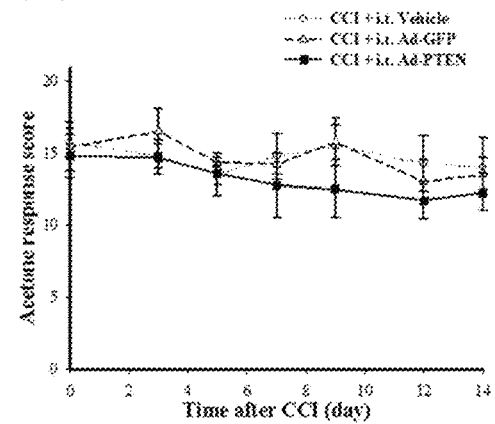

In another embodiment, compared with CCI plus i.t. vehicle group of rats and CCI plus i.t. Ad-GFP group of rats, the CCI-induced development of pain behaviors is significantly prevented by i.t. injection of Ad-PTEN, wherein the pain behaviors include thermal hyperalgesia, mechanical allodynia, cold allodynia, and accompanied weight-bearing deficits (FIG. 5). The result shows that upregulation of PTEN has analgesic effects. It also shows that normal hindpaws of the CCI group of rats do not show any pain-related behaviors (FIG. 6).

Figure 7:
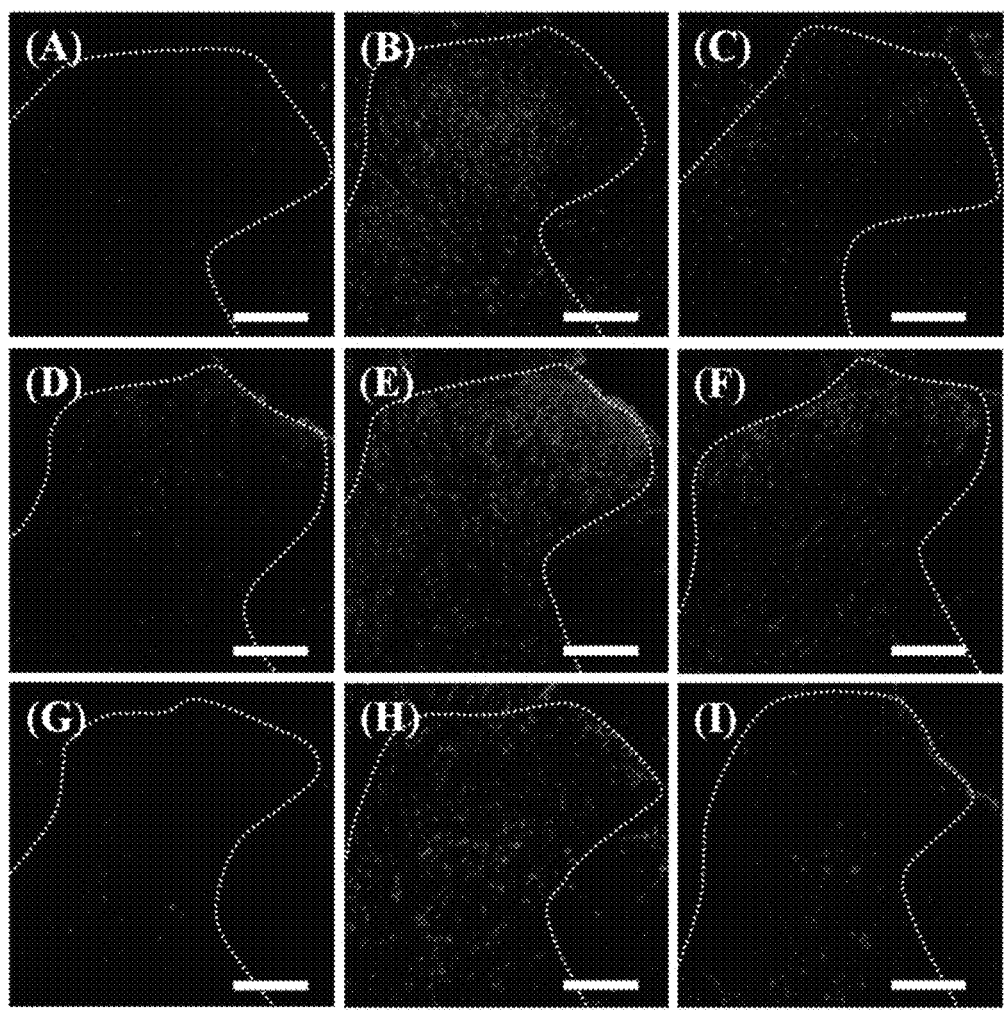
FIG. 7 shows the effects of i.t. Ad-PTEN on CCI-induced microglial and astrocytic activation and upregulation of TNF-α, wherein (A)-(C) respectively show immunostaining images of cells labeled with OX-42 from sham-operated plus i.t. vehicle group (A), CCI plus i.t. Ad-GFP group (B), and CCI plus i.t. Ad-PTEN group (C); (D)-(F) respectively show immunostaining images of cells labeled with GFAP from sham-operated plus i.t. vehicle group (D), CCI plus i.t. Ad-GFP group (E), and CCI plus i.t. Ad-PTEN group (F); (G)-(I) respectively show immunostaining images of cells labeled with TNF-α from sham-operated plus i.t. vehicle group (G), CCI plus i.t. Ad-GFP group (H), and CCI plus i.t. Ad-PTEN group (I). Scale bars: 200 µm for all images. (J)-(L) are bar graphs of quantification of OX-42 (J) and GFAP (K), and TNF-α (L) immunoreactivity; *$P<0.05$ compared with sham-operated plus i.t. vehicle group; #$P<0.05$ compared with CCI plus i.t. Ad-GFP.
Figure 7:
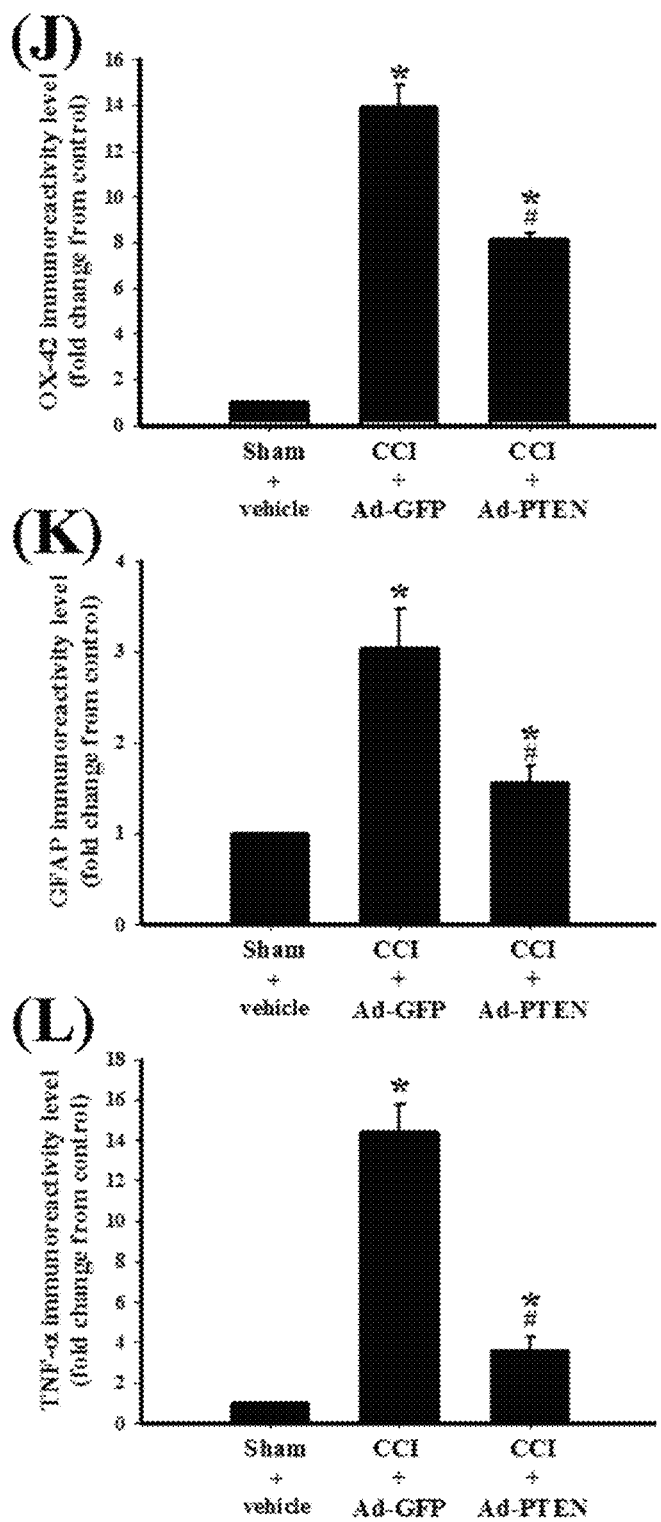

In one embodiment, compared with CCI plus i.t. Ad-GFP group of rats, i.t. injection of Ad-PTEN significantly attenuates CCI-induced neuroinflammation, including microglial (OX-42 is its biomarker) and astrocytic (GFAS is its biomarker) activation and increased expression of TNF-α. The result shows that upregulation of PTEN can decrease spinal neuroinflammation (FIG. 7). Previous studies indicate that the neuroinflammation is associated with the development and maintenance of neuropathic pain.

Figure 8:
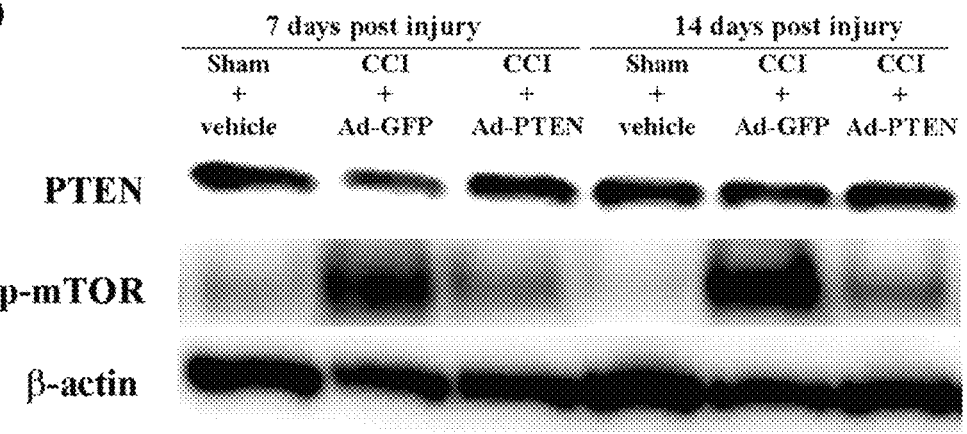
FIG. 8 shows effects of the time course of i.t. Ad-PTEN on the spinal PTEN and phospho-mTOR levels in CCI group of rats, wherein (A) shows Western blots for PTEN, phospho-mTOR, and β-actin proteins; (B)-(C) respectively show relative density of the immunoblot of PTEN (B) and of phospho-mTOR (C). *$P<0.05$: compared with sham-operated plus i.t. vehicle 7 days post injury group; #$P<0.05$: between CCI plus i.t. Ad-PTEN group compared with the same time points in CCI plus i.t. Ad-GFP group.
Figure 8:
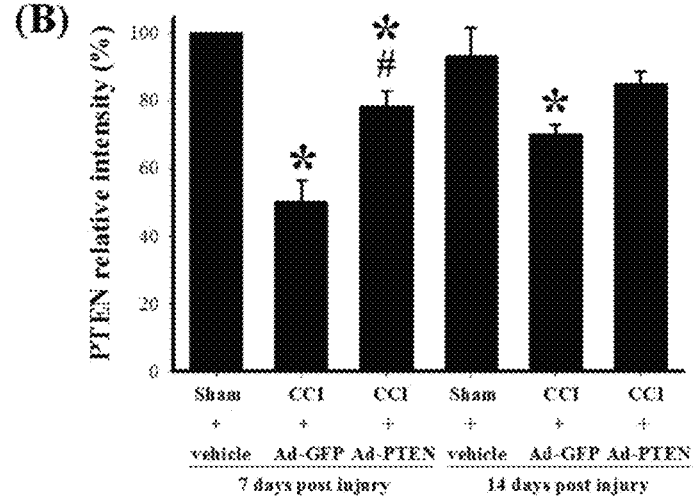
Figure 8:
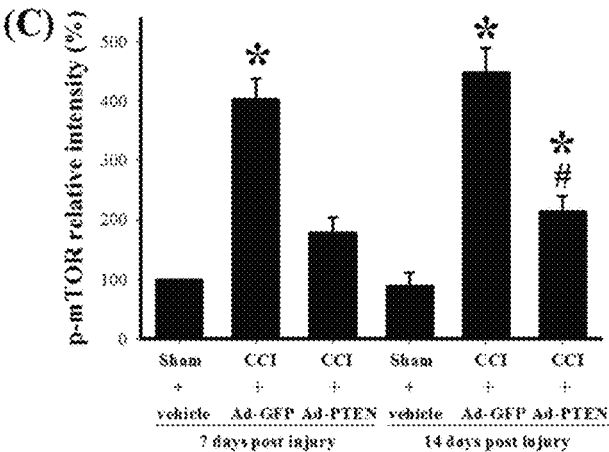
Figure 9:
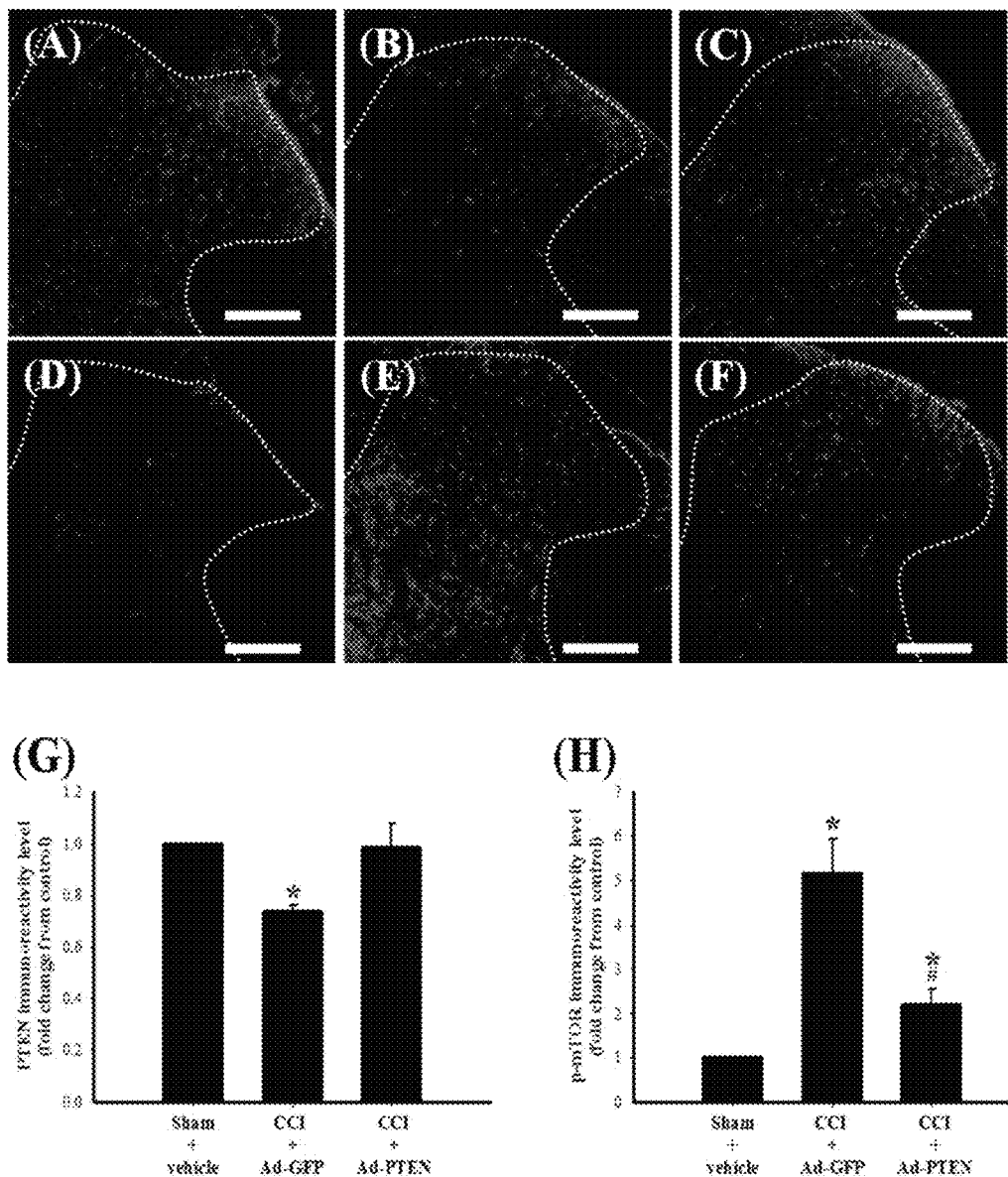
FIG. 9 shows the inhibitive effect of i.t. Ad-PTEN on CCI-induced downregulation of PTEN and upregulation of phospho-mTOR, wherein (A)-(C) are respectively immunostaining images of PTEN from sham-operated plus i.t. vehicle group (A), CCI plus i.t. Ad-GFP group (B), and CCI plus i.t. Ad-PTEN group (C); (D)-(F) are respectively immunostaining images of phospho-mTOR from sham-operated plus i.t. vehicle group (D), CCI plus i.t. Ad-GFP group (E), and CCI plus i.t. Ad-PTEN group (F). Scale bars: 200 µm for all images. (G)-(H) are respectively bar graphs of quantification of PTEN (G) and phospho-mTOR (H) immunoreactivity. *$P<0.05$: compared with sham-operated plus i.t. vehicle group; #$P<0.05$: compared with CCI plus i.t. Ad-GFP.

In another embodiment, compared with CCI plus i.t. Ad-GFP group of rats, i.t. injection of Ad-PTEN significantly attenuates CCI-induced upregulation of phospho-mTOR (FIG. 8 and FIG. 9). Previous studies indicate that the inhibition of mTOR pathway of neuropathic rats can have pain treatment effects.

Figure 10:
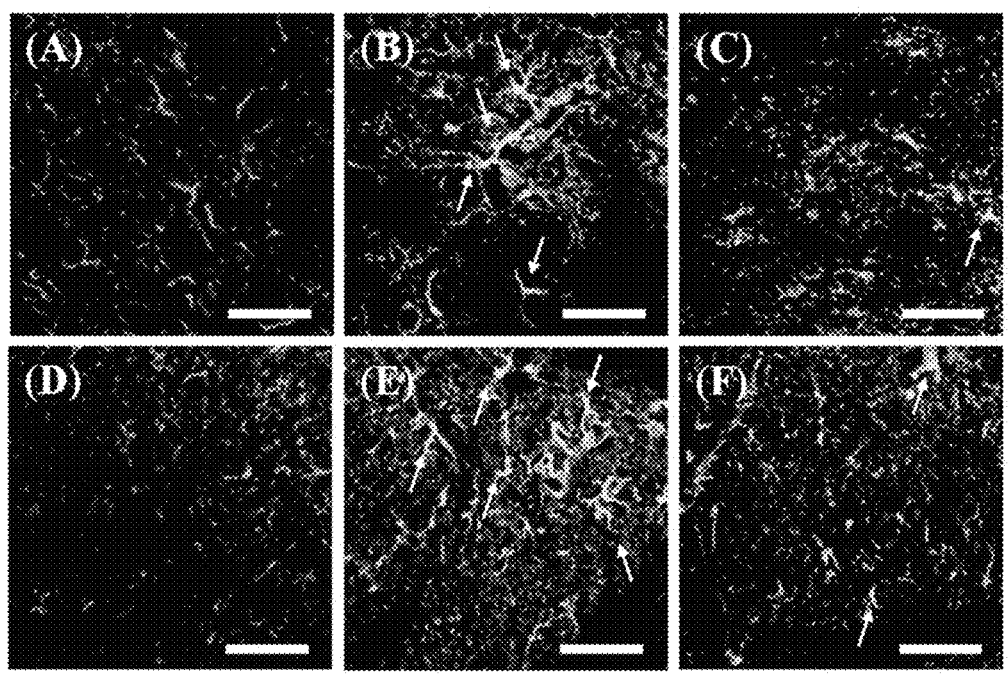
FIG. 10 shows the effects of i.t. Ad-PTEN on CCI-induced upregulation of TNF-α and phospho-mTOR in spinal astrocytes; wherein (A)-(C) are respectively confocal double-immunofluorescent stainings of TNF-α with GFAP from sham-operated plus i.t. vehicle group (A), CCI plus i.t. Ad-GFP group (B), and CCI plus i.t. Ad-PTEN group (C); (D)-(F) are respectively confocal double-immunofluorescent stainings of phospho-mTOR with GFAP from sham-operated plus i.t. vehicle group (D), CCI plus i.t. Ad-GFP group (E), and CCI plus i.t. Ad-PTEN group (F). Scale bars are 50 µm for all images.

In another embodiment, in CCI group of rats, the CCI-induced upregulation of phospho-mTOR and TNF-α are primarily co-localized with astrocytes, and the upregulation is inhibited by i.t. injection of Ad-PTEN (FIG. 10).

Figure 11:
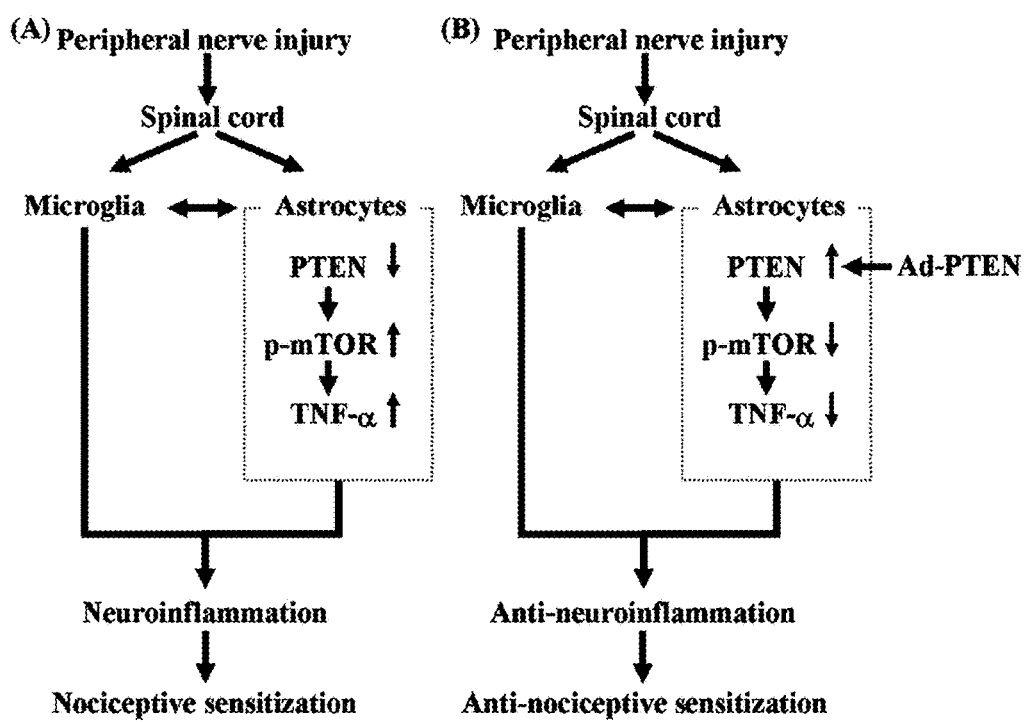
FIG. 11 shows schematic representation of the possible mechanisms of PTEN involvement in neuropathic pain, wherein (A) shows the downregulation of PTEN and the upregulation of phospho-mTOR and TNF-α caused by peripheral nerve injury; (B) shows the upregulation of spinal astrocytic PTEN caused by i.t. Ad-PTEN.

According to the results of the present invention, after i.t. injection of Ad-PTEN, upregulation of spinal astrocytic PTEN inhibits the upregulation of phospho-mTOR and TNF-α, which are caused by the downregulation of astrocytic PTEN, and suppresses the astrocyte-microglia interaction, thereby inhibiting neuroinflammation and nociceptive sensitization (FIG. 11).

In one embodiment, the pain treatment effects result from PTEN by attenuating neuroinflammation or attenuating upregulation of phospho-mTOR.

In one embodiment, attenuating neuroinflammation is to attenuate microglia and astrocyte activation and/or to attenuate upregulation of TNF-α.

A method for screening pharmaceutical compositions having an anti-pain effect, comprising the steps of: (a) providing a neuropathic pain specimen; (b) delivering a pharmaceutical composition into the neuropathic pain specimen; (c) detecting the difference of the PTEN expressions in the neuropathic pain specimen before and after delivering the pharmaceutical composition into the neuropathic pain specimen, wherein an upregulation of PTEN represents that the pharmaceutical composition has an anti-pain effect.

In the present invention, the specimen is a neuropathic specimen, wherein the specimen includes, but is not limited to, a specimen wherein upregulation of PTEN has anti-pain effects, wherein the specimen includes, but not limited to, a living animal, its tissues or cells.

In one embodiment, the method for inducing neuropathic pain is CCI.

In one embodiment, the delivering method is i.t. injection.

The delivering methods of the present invention include, but are not limited to, i.t. injection, oral administration, intramuscular injection, intraperitoneal injection, subcutaneous injection, intravenous injection etc.

In one embodiment, the anti-pain effect is to inhibit or to alleviate pain.

EXAMPLES

The following Examples provide detailed description, which are the best modes provided by the present invention, only used for representing the different aspects and characters of the present invention, and therefore should not be construed as the limitation of the claims.

Experimental Materials and Methods

Animals

The rat model used was male Wistar rats (260 to 285 g), which were housed for free access to food and water in a temperature-controlled (22° C.±1° C.) and light-cycle-controlled (12-h light/12-hdark) room. After the approval of the National Sun Yatsen University and Use Committee, the Guiding Principles in the Care and Use of Animals of the American Physiology Society was conformed to use rats throughout the experiments. For surgery and drug injections, all rats were anesthetized under isoflurane inhalation (2%). Then, for preventing infection during the surgery, all rats received intramuscularly postoperative injection of veterin (cefazolin; 0.17 g/kg). Our every effort in experimental design and execution was for the purpose of minimizing the suffering and number of rats we used.

Induction of Peripheral Mononeuropathy by CCI

As described in previous studies (Bennett G J and Xie Y K., *Pain.*, 33:87-107 (1988); Lin Y C et al., *Behav Pharmacol.*, 22: 739-50 (2011); Jean Y H et al., *Br J Pharmacol.*, 158:713-25 (2009)), the surgery of CCI was performed on the right sciatic nerve of rats, to expose the right sciatic nerve of rats (at mid-thigh level), to dissect a 5-mm-long nerve segment of the sciatic nerve, to place four loose ligatures (4 to 0 chromic gut) around the sciatic nerve (with 1-mm intervals), and then to suture muscle and skin incision layer by layer. For the sham-operated rats, the surgery was performed only to expose the right sciatic nerve but without ligation.

Implantation of i.t. Catheters

Using the method described in previous studies (Yaksh T L and Rudy T A., *Physiol Behav.*, 17:1031-6 (1976); Lin Y C et al., *Behav Pharmacol.*, 22:739-50 (2011); Jean Y H et al., *Br J Pharmacol.*, 158:713-25 (2009)), i.t. catheter was inserted (PE5 tubes: 9-cm long, 0.008-in. inner diameter, 0.014-in. outer diameter; Spectranetics, Colorado Springs, Colo., USA) to the lumbar enlargement of the spinal cord via the atlanto-occipital membrane at the base of the rat's skull down, and then externalized and fixed one end of the i.t. catheter to the cranial aspect of the rat's head for spinal drug administration.

Because the dead volume of i.t. catheter was 3.5 µL, to ensure complete drug delivery, an i.t. artificial cerebrospinal fluid (aCSF) flush (10 µL) followed all i.t. injections. The composition of aCSF was as follows: 151.1 mM $Na^+$, 2.6 mM $K^+$, 1.3 mM $Ca^{2+}$, 0.9 mM $Me^+$, 122.7 mM $Cl^-$, 21.0 mM $HCO_3^-$, 2.5 mM $HPO_4^{2-}$, and 3.5 mM dextrose and bubbled with 5% $CO_2$ in 95% $O_2$ for adjusting the final pH to 7.3. Five days after implantation of i.t. catheters, rats with i.t. catheter that had the fresh blood in the CSF or exhibit of gross neurological injury from the following experiments were excluded. According to the method described in previous studies (Hains B C and Waxman S G, *J Neurosci.*, 26:4308-17 (2006); Lin Y C et al., *Behav Pharmacol.*, 22:739-50 (2011); Jean Y H et al., *Br J Pharmacol.*, 158: 713-25 (2009)), the locomotor function of rats was evaluated using the Basso, Beattie, and Bresnahan (BBB) locomotor scale.

Preparation of Adenovirus Vectors

Using the method described in our previous studies (Kung M L et al., *Biochem Biophys Res Commun.*, 425:169-76 (2012); Kuo H M et al., *Atherosclerosis.*, 221:341-9 (2012); Wang C R et al., *Arthritis Rheum.*, 58: 1650-6 (2008)), E1- and E3-defective recombinant adenovirus vectors encoding green fluorescent protein (Ad-GFP), PTEN antisense oligonucleotide (Ad-antisense PTEN), or human PTEN cDNA (Ad-PTEN) were prepared. These adenovirus solutions were tittered with a plaque-forming assay, aliquoted, and then stored at −80° C. before their use.

Amount of PTEN Measured in the i.t. Injection

In one experiment, the amount of PTEN measured in the i.t. injection of rats was represented by from $5 \times 10^8$ to $2 \times 10^9$ plaque forming units of adenovirus vectors. In another experiment, the amount of PTEN measured in the i.t. injection of rats was represented by from $6.67 \times 10^8$ to $1.5 \times 10^9$ plaque forming units of adenovirus vectors. In another experiment, the amount of PTEN measured in the i.t. injection of rats was represented by from $8 \times 10^8$ to $1.25 \times 10^9$ plaque forming units of adenovirus vectors. In another experiment, the amount of PTEN measured in the i.t. injection of rats was represented by $1 \times 10^9$ plaque forming units of adenovirus vectors.

Data and Statistical Analysis

All data are shown as means±standard error on the mean (SEM). For statistical analysis, differences between groups of rats were calculated by a one-way analysis of variance (ANOVA), used the Student-Newman-Keuls post hoc test, and then defined the criterion for statistical significance as $P<0.05$.

Example 1: Nociceptive Behavioral Testing

The Nociceptive behavioral testing comprised (i) a thermal hyperalgesia test, (ii) a mechanical allodynia test, (iii) a cold allodynia test, and (iv) a weight-bearing test.

(i.) Thermal Hyperalgesia Test:

After each rat was placed into each compartment of clear plastic cages onto an elevated glass platform, then an IITC analgesiometer was used (IITC Inc., Woodland Hills, Calif., USA) to test thermal hyperalgesia as described by previous studies (Hargreaves K et al., *Pain.*, 32:77-88 (1988); Jean Y H et al., *Eur J Pharmacol.*, 578:323-31 (2008); Huang S Y et al., *Mar Drugs.*, 10:1899-919 (2012)) to position a radiant heat source with low-intensity heat (active intensity=25) onto the middle of the plantar surface of the rat, with a cutoff time of 30 seconds (s), to measure the PWL (in seconds) of the rat until the rat showed a positive sign of pain behavior (licking or withdrawal).

(ii.) Mechanical Allodynia Test:

After each rat was set into each compartment of clear plastic cages onto an elevated metal mesh floor for easy access to the rats' paws, PWT (in g) was measured to assess mechanical allodynia as described by previous studies (Chaplan S R et al., *J Neurosci Methods.*, 53:55-63 (1994); Huang S Y et al., *Mar Drugs.*, 10:1899-919 (2012); Lin Y C et al., *Behav Pharmacol.*, 22:739-50 (2011)). The test was measured using calibrated von Frey filaments (Stoelting, Wood Dale, Ill., USA). Then, a series of von Frey filaments of logarithmically incremental stiffness were applied to the midplantar region of the rat hindpaw by Chaplan's 'up-down' method to determine the closest filament to the threshold of pain response (licking or withdrawal) of the rat.

(iii.) Cold Allodynia Test:

As described by the previous study (Huang S Y et al., *Mar Drugs.*, 10: 1899-919 (2012)), after each rat was placed in the individual plastic compartments on an elevated metal mesh floor, cold allodynia response of the rat was monitored during 1 min following acetone stimulus (25 µl) onto the center of the plantar surface of rats' hindpaw.

Modified from 4-point scale of previous studies (Bardin L et al., *Behav Brain Res.*, 205:360-6 (2009); Flatters S J et al., *Pain.*, 109:150-61 (2004)), acetone response scores of the paw were graded according to a 6-point scale: 0, repeated flicking with persistent licking in 2 seconds (s) following acetone stimulus; 1, prolonged withdrawal or repeated flicking in 2 s following acetone stimulus; 2, quick and more violent withdrawal, flick, or stamp in 2 s following acetone stimulus; 3, quick withdrawal, flick, or stamp in 2 s following acetone stimulus; 4, withdrawal, flick, or stamp more than 2 s following acetone stimulus; and 5, no response. Then, the four individual scores were summed up for obtaining acetone response score of the paw of each rat. The minimum possible total score of the paw could be 0 point (the rat exhibited repeated flicking and licking of paws on each of the four trials), and the maximum possible total score of the paw could be 20 points (the rat exhibited no response to any of the four trials).

(iv.) Weight-Bearing Test:

The rat placed its hindpaws onto the two force transducers of the incapacitance tester (Singa Technology Corporation, Taoyuan) for measuring the hindpaw weightbearing deficits (change in hindpaw weight distribution; in g) as described by previous studies (Huang S Y et al., *Mar Drugs.*, 10:1899-919 (2012); Wen Z H et al., *Osteoarthritis Cartilage.*, 18:1192-202 (2010)). Under normal conditions, the naïve rat distributed weight equally between both hind limbs, but after inducing inflammation of one hind limb like CCI, the rat redistributed weight for lowering weight-bearing of the affected limb Change in hindpaw weight distribution of the rat was expressed as a difference by subtracting the affected limb (the right hind limb; the ipsilateral side; injured side) from the normal limb (the left hind limb; the contralateral side; normal side) measured at the same time.

Example 2: Spinal Immunohistofluorescence Analysis

For reducing variations in immunohistochemical procedures, the lumbar spinal tissues from different groups of rats were mounted into the same OCT block, these spinal tissues were sectioned together using a cryostat at −30° C. (HM550; Microm, Waldorf, Germany) and performed the following spinal immunohistofluorescence analysis, with a modified method described by previous studies (Sung B et al., *J Neurosci.*, 23:2899-910 (2003); Huang S Y et al., *Mar Drugs.*, 10: 1899-919 (2012); Jean Y H et al., *Br J Pharmacol.*, 158:713-25 (2009)).

The spinal sections (10 µm) were incubated with primary antibody overnight at 4° C., wherein the antibody included anti-phosphorylated PTEN (anti-phospho-PTEN; Ser380) (1:200 dilution, cat. 9551; Cell Signaling Technology Inc., Beverly, Mass., USA; polyclonal rabbit antibody), anti-PTEN (1:200 dilution, cat. 10005059; Cayman Chemical, Ann Arbor, Mich., USA; polyclonal rabbit antibody), anti-phosphorylated mTOR (anti-phospho-mTOR; Ser2448) (1:200 dilution, cat. 2976; Cell Signaling Technology Inc., Beverly, Mass., USA; polyclonal rabbit antibody), anti-OX-42 (CD11b, microglial marker, 1:200 dilution, cat. CBL1512; EMD Millipore, Temecula, Calif., USA; monoclonal mouse antibody), anti-glial fibrillary acidic protein (GFAP) (astrocytic marker, 1:200 dilution, cat. MAB3402; EMD Millipore, Temecula, Calif., USA; monoclonal mouse antibody), or anti-TNF-α (1:200 dilution, cat. ARC3012; Life Technologies Corporation, Grand Island, N.Y., USA).

This was then followed by Alexa Fluor 488-labeled chicken anti-mouse IgG antibody (1:400 dilution, cat. A-21200; Molecular Probes, Eugene, Oreg., USA; green fluorescence) or DyLight 549-conjugated donkey anti-rabbit IgG antibody (1:400 dilution, cat. 711-506-152; Jackson ImmunoResearch Laboratories Inc., West Grove, Pa., USA; red fluorescence) for 40 min at room temperature.

For immunostaining analysis, a Leica DM-6000 CS fluorescence microscope was used (Leica Instruments Inc., Wetzlar, Germany) for examination of these stained spinal sections, and then a SPOT Xplorer Digital camera (Diagnostic Instruments, Inc., Sterling Heights, Mich., USA) was used for photographing all immunofluorescence images of phospho-PTEN, PTEN, phospho-mTOR, OX-42, GFAP, and TNF-α, respectively. The pixel values of the immunoreactivepositive area (using three sections per rat) were measured by Image J software (National Institutes of Health, Bethesda, Md., USA).

Spinal neurons located in the superficial laminae, laminae I to III, responded to nociceptive stimuli and directly participated in the transmission of nociception to the brain, and thereby the superficial laminae played a more important role in neuropathic pain than the deep laminae. Therefore, in accordance to the method used for neuropathic rodents (Raposo D et al., *Brain Res Bull.*, 110:68-75 (2015); Chen N F et al., *Mar Drugs.*, 12:3792-817 (2014); Stokes J A et al., *J Neuroinflammation.*, 10:148 (2013); Kawasaki Y et al., *Nat Med.*, 14:331-6 (2008)), the focus was placed on quantifying the immunoreactivity of the targeted protein in the superficial laminae of the spinal cord. The immunofluorescence data were expressed as a percentage change compared to sham-operated or sham-operated plus i.t. vehicle group, which were considered to be 100%.

For double-immunofluorescent staining of PTEN and neuronal marker, the spinal sections were incubated with a mixture of anti-PTEN (1:200 dilution) and anti-Neuronal Nuclei (NeuN) (neuronal-specific nuclear protein; neuronal marker, 1:500, Alexa Fluor 488 conjugated antibody, cat. MAB377X, EMD Millipore, Temecula, Calif., USA; monoclonal mouse antibody) antibodies overnight at 4° C., and then followed by DyLight 549-conjugated anti-rabbit IgG antibody (1:400 dilution) for 40 min at room temperature.

For double-immunofluorescent staining of PTEN and microglial marker or astrocytic marker, the spinal sections were incubated with a mixture of anti-PTEN (1:200 dilution) and OX-42 (1:200 dilution) or GFAP (1:200 dilution) antibodies overnight at 4° C., and then followed by a mixture of Alexa Fluor 488-conjugated anti-mouse IgG antibody (1:400 dilution) and DyLight 549-conjugated anti-rabbit IgG antibody (1:400 dilution) for 40 min at room temperature.

For double-immunofluorescent staining of anti-TNF-α or phospho-mTOR and astrocytic marker, the spinal sections were incubated with a mixture of anti-TNF-α (1:200 dilution) or anti-phospho-mTOR (1:200 dilution) and GFAP (1:200 dilution) antibodies overnight at 4° C., and then followed by a mixture of DyLight 549-conjugated anti rabbit IgG antibody (1:400 dilution) and Alexa Fluor 633-conjugated goat anti-mouse IgG antibody (1:400 dilution, cat. A21052; Life Technologies Corporation) for 40 min at room temperature.

The double-immunostaining images were examined and acquired with Leica TCS SP5 II confocal microscope (Leica Instruments Inc., Wetzlar, Germany). the color of TNF-α or phospho-mTOR for 549-nm excitation line was set as pseudo red and the color of GFAP for 633 nm excitation line was set as pseudo green. When co-localization of two proteins occurred, the merge of above two colors, pseudo red (TNF-α or phosphomTOR) and pseudo green (GFAP), yielded yellow color.

Example 3: Western Blot Analysis

Following the published method (Chen N F et al., *J Pain.*, 14:1671-85 (2013); Jean Y H et al., *Eur J Pharmacol.*, 578:323-31 (2008); Chen W F et al., *Neuroscience.*, 165: 1217-32 (2010)), Western blotting analysis was performed on the affected side of the lumbar spinal dorsal samples from the rats. For Western blotting analysis, spinal dorsal samples from rats were collected and washed with ice-cold PBS, and then a Polytron homogenizer (5 cycles of 10 s at 3,000 rpm) was used to homogenize in ice-cold lysis buffer (1 μg/ml aprotinin, 50 mM Tris, 150 mM NaCl, 100 μg/ml phenylmethylsulfonyl fluoride, 1% Triton X-100, pH 7.5). After centrifuging at 20,000×g for 60 min at 4° C., this supernatant was retained for Western blot analysis of phospho-PTEN and PTEN.

Modified from the method of Lowry et al. (Lowry O H et al., *J Biol Chem.*, 193:265-75 (1951)), the protein concentrations of the supernatant were determined with the DC protein assay kit (Bio-Rad, Hercules, Calif., USA). An equal volume of sample buffer was added to the supernatant, wherein the sample buffer comprised 2% 2-mercaptoethanol, 10% glycerol, 0.1% bromophenol blue, 50 mM Tris-HCl, pH 7.2, and 2% sodium dodecyl sulfate (SDS).

Then, the proteins of supernatant were electrophoresed through a tricine SDS-polyacrylamide gel at 150 V for 90 min and the proteins within the gel were transferred to a polyvinylidene difluoride membrane (PVDF membrane; Immobilon-P, Millipore, 0.45-μM pore size) in transfer buffer at 125 mA overnight at 4° C., wherein the transfer buffer comprised 380 mM glycine, 1% SDS, 50 mM Tris-HCl, 20% methanol.

With blocking PVDF membrane for 1 h at room temperature using 5% non-fat dry milk in Tris-buffered saline (TTBS), wherein the TTBS comprised 137 mM NaCl, 0.1% Tween 20, 20 mM Tris-HCl, pH 7.4. Then the PVDF membrane was incubated with antibodies against phospho-PTEN (Ser380; 1:1,000 dilution) or PTEN (1:1,000 dilution) proteins for 180 min at room temperature. The antibodies recognized immunoreactive bands of phospho-PTEN (approximately 54 kDa) and PTEN (approximately 47 kDa) protein, which were visualized with enhanced chemiluminescence (ECL kit; Millipore) and photographed using the UVP BioChemi imaging system (UVP LLC, Upland, Calif., USA), respectively.

Finally, the relative densitometric quantification of the immunoreactive bands of phospho-PTEN and PTEN protein was performed with LabWorks 4.0 software (UVP LLC, Upland, Calif., USA), and relative variations between the bands of the sham-operated or sham-operated plus i.t. vehicle group and the other groups were calculated using the same image. In addition, the PVDF membranes were reprobed using an anti-β-actin antibody (1:2,500 dilution; catalog no. A5441; Sigma Co., Ltd., St Louis, Mo., USA; monoclonal mouse antibody), which was the loading control to verify the equivalent amounts of protein which were loaded in each lane.

Results

1. The Time Course of Changes of Endogenous Spinal PTEN in Neuropathic Rats

To explore any potential changes in the spinal PTEN pathway in neuropathic rats, the lumbar spinal tissues from the following eight groups of rats were prepared: (1) 1 day after sham operation, (2) 3 days after sham operation, (3) 7 days after sham operation, (4) 14 days after sham operation, (5) 1 day after CCI, (6) 3 days after CCI, (7) 7 days after CCI, and (8) 14 days after CCI. A spinal immunohistofluorescence analysis using three antibodies against phospho-PTEN (red, FIG. 1 (A)-(C)), PTEN (green, FIG. 1. (D)-(F)), and phospho-mTOR (red, FIG. 1 (G)-(I)) was performed to evaluate the expression of the PTEN pathway in the affected side of the lumbar spinal dorsal gray matter in neuropathic rats.

Compared with the sham-operated group (FIG. 1 (A), (D)), immunoreactivity increased for phospho-PTEN but decreased for PTEN, 7 days (FIGS. 1 (B), (E)) and 14 days (FIG. 1 (C), (F)) after CCI. Similar to the findings in a previous study (Zhang W, et al., Pharmacol Biochem Behav., 111:64-70 (2013)), phospho-mTOR immunoreactivity increased 7 days (FIG. 1 (H)) and 14 days (FIG. 1 (I)) after CCI, as compared with that of the sham-operated group (FIG. 1 (G)). Quantification of the immunoreactivity results further confirmed phospho-PTEN (FIG. 1 (J)) and phospho-mTOR (FIG. 1 (L)) upregulation, as well as PTEN downregulation (FIG. 1 (K)), 3 days, 7 days, and 14 days after CCI. CCI significantly upregulated spinal immunoreactivity of phospho-PTEN and phospho-mTOR and downregulated spinal PTEN immunoreactivity.

The description of FIG. 1:

FIG. 1 (A)-(C) were immunostaining images, illustrating cells labeled with phosphor-PTEN (red) in Spinal cord sections (10 μm) from the sham-operated group (FIG. 1 (A)), 7 days after CCI group (FIG. 1 (B)), and 14 days after CCI group (FIG. 1 (C)) respectively. Scale bars were 200 μm.

FIG. 1(D)-(F) were immunostaining images, illustrating cells labeled with PTEN (green) in Spinal cord sections (10 μm) from the sham-operated group (FIG. 1 (D)), 7 days after CCI group (FIG. 1 (E)), and 14 days after CCI group (FIG. 1 (F)) respectively. Scale bars were 200 μm.

FIG. 1 (G)-(I) were immunostaining images, illustrating cells labeled with phospho-mTOR (red) in Spinal cord sections (10 μm) from the sham-operated group (FIG. 1 (G)), 7 days after CCI group (FIG. 1 (H)), and 14 days after CCI group (FIG. 1 (I)) respectively. Scale bars were 200 μm FIG. 1 (J)-(L) were bar graphs of quantification of phospho-PTEN (FIG. 1 (J)), PTEN (FIG. 1 (K)), and phospho-mTOR (FIG. 1 (L)) immunoreactivity respectively in the affected side of dorsal horn of the lumbar spinal gray matter 1, 3, 7, and 14 days after CCI as compared with sham-operated rats. Each bar in panels represents the mean±SEM; *$P<0.05$ compared with the sham-operated group.

Further, Western blot analysis was used to verify changes in endogenous PTEN in the dorsal horn of the lumbar spinal cord (FIG. 2 (A)). The Western blot analysis revealed upregulation of phospho-PTEN (FIG. 2 (B)) and downregulation of PTEN (FIG. 2 (C)) 14 days after CCI surgery. Western blotting of spinal dorsal horn tissue homogenate revealed that phospho-PTEN and PTEN protein expression was detectable in the sham-operated group, but CCI evoked upregulation of phospho-PTEN protein and downregulation of PTEN protein 14 days after CCI. Western blotting of β-actin was performed to verify the equivalent amounts of protein were loaded in each lane.

The description of FIG. 2:

FIG. 2 (A) showed Western blots for phospho-PTEN, PTEN, and β-actin proteins from sham-operated and 14 days after CCI groups; FIG. 2 (B) showed relative density of immunoblot of phospho-PTEN; FIG. 2 (C) showed relative density of immunoblot of PTEN, in which relative band intensities of phospho-PTEN and PTEN were quantified by densitometry and indicated as the percent change relative to that for the sham-operated group (100%). Each bar of FIGS. 2 (B) and 2 (C) represented the mean±SEM with three rats per group. *P<0.05 compared with sham-operated group.

FIG. 2 (D)-(F) were confocal double-immunofluorescent staining images of PTEN (red) with NeuN (neuronal-specific marker; green) (FIG. 2 (D)), GFAP (astrocyte specific marker; green) (FIG. 2 (E)) or OX-42 (microglial specific marker; green) (FIG. 2 (F)) in the dorsal horn region of the lumbar spinal cord of sham-operated group. The merged images of FIG. 2 (D)-(F) (yellow; white arrow) indicated co-localization of PTEN with NeuN, GFAP, and OX-42 immunoreactive cells in the spinal cord, respectively. Scale bars were 50 μm for all images.

To examine the cellular specificity of endogenous PTEN in the dorsal horn of the lumbar spinal cord, lumbar spinal tissues from the sham-operated group were prepared for double-immunofluorescent staining. Confocal double-immunostaining images of the lumbar spinal dorsal gray matter of sham-operated rats further confirmed that most PTEN signals were more often co-localized with GFAP-positive cells (astrocytes, FIG. 2 (E)) than NeuN-positive (neuronal cells; FIG. 2 (D)) or OX-42-positive cells (microglial cells, FIG. 2 (F)).

2. The Effect of i.t. Ad-Antisense PTEN on Nociceptive Responses

To explore the effects of modulating spinal PTEN pathway on nociceptive behaviors in normal rats, the following five groups of rats were prepared: (1) naïve, (2) i.t. vehicle, (3) i.t. Ad-GFP, (4) i.t. Ad-antisense PTEN, and (5) i.t. Ad-PTEN. Five days after implantation of the i.t. catheters, the rats received i.t. injection of vehicle, Ad-GFP, Ad-antisense PTEN, or Ad-PTEN.

No significant differences were observed between the naïve group (data not shown) and the i.t. vehicle group for PWL, PWT, or acetone response scores. Compared with i.t. vehicle group, i.t. Ad-GFP did not significantly affect PWL (FIG. 3 (A)), PWT (FIG. 3 (B)), and acetone response score (FIG. 3 (C)) of rats. After i.t. injection of Ad-antisense PTEN, the rats exhibited mechanical allodynia (FIG. 3 (B)) but not thermal hyperalgesia (FIG. 3 (A)) and cold allodynia (FIG. 3 (C)) from 3 to 7 days compared with that of i.t. Ad-GFP group. Compared with i.t. Ad-GFP group, i.t. Ad-PTEN did not significantly affect PWL (FIG. 3 (A)), PWT (FIG. 3 (B)), and acetone response score (FIG. 3 (C)) of rats. In addition, in the present invention, i.t. Ad-GFP, Ad-antisense PTEN, or Ad-PTEN-treated rats did not exhibit any obvious abnormal external behavior (including locomotor function).

FIG. 3 (A)-(C) showed the time course of the effects of i.t. Ad-antisense PTEN on nociceptive behaviors, including thermal hyperalgesia (FIG. 3 (A)), mechanical allodynia (FIG. 3 (B)) and cold allodynia (FIG. 3 (C)). Each point represented the mean±SEM with six rats per group. *P<0.05 compared with vehicle group.

3. The Inhibitory Effects of Ad-PTEN on Nociception in Neuropathic Rats

To verify that Ad-PTEN has the ability to upregulate the production of spinal PTEN, the following three groups of rats were prepared: (1) naïve plus i.t. vehicle, (2) naïve plus i.t. Ad-GFP, and (3) naïve plus i.t. Ad-PTEN. No significant difference in spinal PTEN expression was observed between naïve rats plus i.t. vehicle (FIG. 4 (A)) and rats examined 14 days after i.t. injection of Ad-GFP (FIG. 4 (B)), whereas PTEN immunoreactivity increased 14 days after i.t. Ad-PTEN (FIG. 4 (C)).

Figure 4:
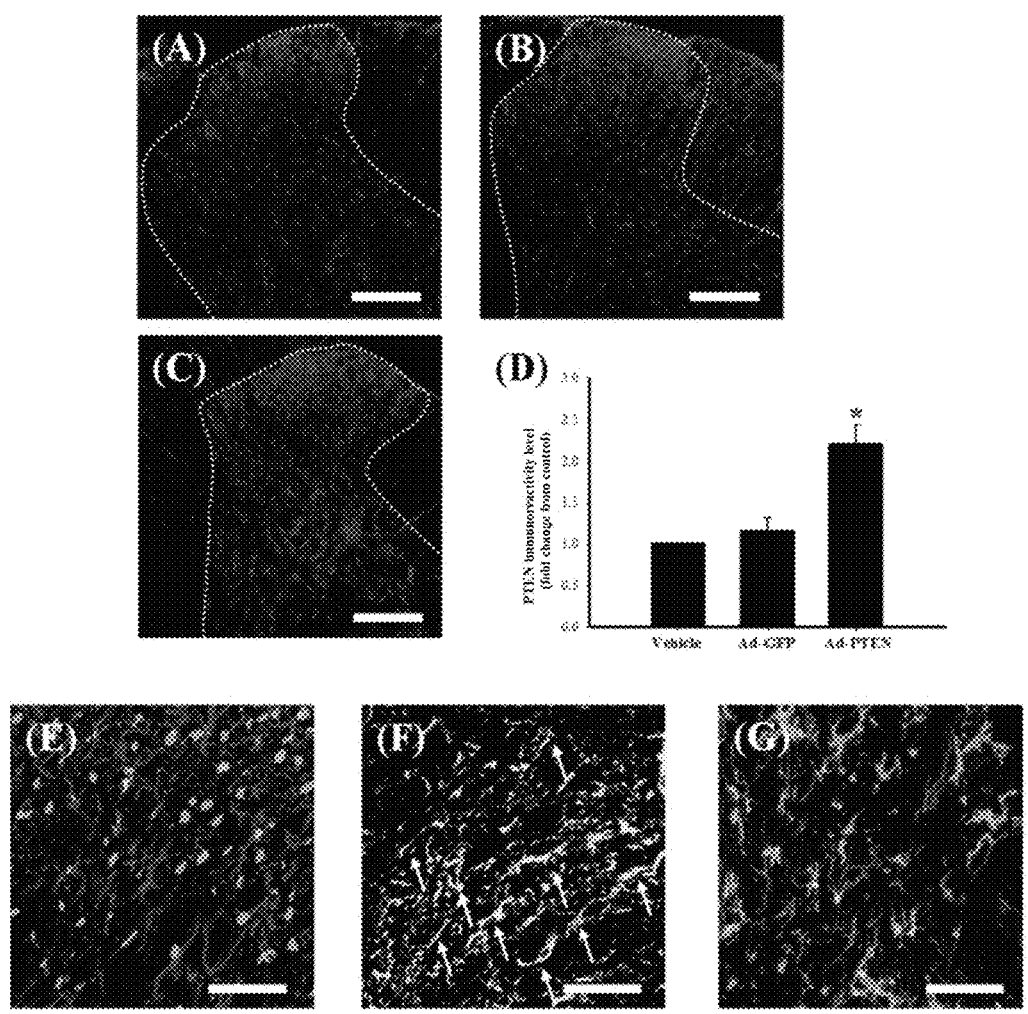
FIG. 4 shows the effects of i.t. injection of Ad-PTEN on PTEN in the dorsal lumbar spinal cord, wherein (A)-(C) are respectively immunostaining images of PTEN from 14 days after i.t. injection of vehicle group (A), Ad-GFP group (B), and Ad-PTEN group (C). Scale bars are 200 µm for panels (A)-(C). (D) is a bar graph of the quantification of PTEN immunoreactivity when compared with i.t. injection of vehicle group; *$P<0.05$ compared with the vehicle group. (E)-(G) are respectively confocal double-immunofluorescent staining images of PTEN with NeuN (E), GFAP (F) and OX-42 (G) from the i.t. Ad-PTEN group. Scale bars are 50 µm for panels (E)-(G).

Quantification of the immunoreactivity results (FIG. 4 (D)) further confirmed that PTEN upregulation in the naïve plus i.t. Ad-PTEN group 14 days after i.t. injection. Confocal double-immunostaining images of the lumbar spinal dorsal gray matter further confirmed most PTEN signals were more often co-localized with GFAP-positive cells (astrocytes; FIG. 4 (F)) than NeuN-positive (neuronal cells; FIG. 4 (E)) or OX-42-positive cells (microglial cells; FIG. 4 (G)) in the naïve rats administered i.t. Ad-PTEN.

The description of FIG. 4:

FIG. 4 (A)-(C) were immunostaining images, illustrating the cells labeled with PTEN (red) in spinal cord sections (10 μm) fourteen days after i.t. injection of vehicle group (FIG. 4 (A)), Ad-GFP group (FIG. 4 (B)), and Ad-PTEN group (FIG. 4 (C)) respectively. Scale bars were 200 μm. FIG. 4 (D) was a bar graph of quantification of PTEN immunoreactivity in the affected side of dorsal horn of the lumbar spinal gray matter compared with vehicle group. Each bar represented the mean±SEM with six rats per group. *P<0.05 compared with the vehicle group. Injection (i.t.) of Ad-PTEN significantly upregulated spinal PTEN immunoreactivity.

FIG. 4 (E)-(G) showed confocal double-immunofluorescent staining of PTEN (red) with NeuN (neuronal-specific marker; green) (FIG. 4 (E)), GFAP (astrocyte specific marker; green) (FIG. 4 (F)), and OX-42 (microglial specific marker; green) (FIG. 4 (G)) in the dorsal horn region of the lumbar spinal cord of the i.t. Ad-PTEN group. The merged images of FIG. 4 (E)-(G) (yellow; white arrow) indicated co-localization of PTEN with NeuN, GFAP, and OX-42 immunoreactive cells in the spinal cord, respectively. Scale bars were 50 μm. *P<0.05 compared with the vehicle group.

To examine whether spinal PTEN upregulation induced with i.t. Ad-PTEN affected neuropathic pain behaviors, the following three groups of rats were prepared: (1) CCI plus i.t. vehicle, (2) CCI plus i.t. Ad-GFP, and (3) CCI plus i.t. Ad-PTEN. Five days after the i.t. catheters were implanted, the rats underwent CCI surgery, and the vehicle, Ad-GFP, or Ad-PTEN was administered i.t. immediately afterwards.

Similar to previous findings (Shi J Y et al., *Hum Gene Ther.*, 22:721-31 (2011)), CCI promoted the development and maintenance of nociceptive behaviors in rats. Compared with the vehicle group, i.t. Ad-GFP did not significantly affect PWL (FIG. 5 (A)), PWT (FIG. 5 (B)), acetone response score (FIG. 5 (C)), and weight-bearing deficits (FIG. 5 (D)) for the affected hindpaw of CCI rats. Compared with i.t. Ad-GFP group, i.t. Ad-PTEN significantly attenuated CCI-induced thermal hyperalgesia (FIG. 5 (A)), mechanical allodynia (FIG. 5 (B)), cold allodynia (FIG. 5 (C)), and weight-bearing deficits (FIG. 5 (D)) up to 14 days post injury.

The description of FIG. 5:

FIG. 5 (A)-(D) showed the time course of i.t. Ad-PTEN effects on nociceptive behaviors in CCI rats, including thermal hyperalgesia (FIG. 5 (A)), mechanical allodynia (FIG. 5 (B)), cold allodynia (FIG. 5 (C)), and weight-bearing deficits (FIG. 5 (D)). Each point represented the mean±SEM with six rats per group. *P<0.05 compared with CCI plus i.t. vehicle group.

FIG. 6 (A)-(C) showed the effects of i.t. Ad-PTEN on nociceptive behaviors with the normal hindpaw in CCI rats, including thermal hyperalgesia (FIG. 6 (A)), mechanical allodynia (FIG. 6 (B)), and cold allodynia (FIG. 6 (C)) tests. Each point represented the mean±SEM with six rats per group. The result of FIG. 6 was contrasted with the result of FIG. 5, and was similar to previous studies (Austin P J and Wu A, *J Vis Exp.* (2012); Zhang L et al., *Afr J Biotechnol.*, 10:6372-80 (2011)), the normal hindpaw in CCI rats did not show pain-related behavior (FIG. 6). Compared with i.t. vehicle group, neither i.t. Ad-GFP nor Ad-PTEN significantly affected PWL (FIG. 6 (A)), PWT (FIG. 6 (B)), or acetone response scores (FIG. 6 (C)) for the normal hindpaw of CCI rats. In addition, i.t. Ad-GFP- and Ad-PTEN-treated CCI rats failed to show obvious abnormal behaviors (including locomotor function), and the naïve-plus-i.t. Ad-PTEN rats exhibited normal locomotor function.

The present invention then focused on 14 days post injury to determine whether the modulation of spinal neuroinflammatory processes was involved in the maintenance of the antinociceptive effects of the upregulation of spinal PTEN by i.t. Ad-PTEN.

4. The Effect of Ad-PTEN on Spinal Neuroinflammation in Neuropathic Rats

For spinal immunohistofluorescence assay, spinal tissues on day 14 post injury from the following three groups of rats were collected: (1) sham-operated plus i.t. vehicle, (2) CCI plus i.t. Ad-GFP, and (3) CCI plus i.t. Ad-PTEN. OX-42-, GFAP-, and TNF-α-immunoreactive cells were scattered throughout the affected side of dorsal horn of the lumbar spinal gray matter of sham-operated plus i.t. vehicle group (FIG. 7 (A), (D), (G)), CCI plus i.t. Ad-GFP group (FIG. 7 (B), (E), (H)), and CCI plus i.t. Ad-PTEN group (FIG. 7 (C), (F), (I)).

Similarly, as previously reported (Lin Y C et al., *Behav Pharmacol.*, 22:739-50 (2011); Chen N F et al., *J Pain.*, 14:1671-85 (2013)), the immunoreactivity of OX-42 (FIG. 7 (B)), GFAP (FIG. 7 (E)), and TNF-α (FIG. 7 (H)) of CCI plus i.t. Ad-GFP group were upregulated on day 14 post injury when compared with the sham-operated plus i.t. vehicle group. CCI-induced upregulation of OX-42 (FIG. 7 (C)), GFAP (FIG. 7 (F)), and TNF-α (FIG. 7 (I)) were inhibited by i.t. Ad-PTEN. Quantification of OX-42 (FIG. 7 (J)), GFAP (FIG. 7 (K)), and TNF-α (FIG. 7 (L)) immunoreactivity supported the finding that the inhibition of CCI-induced upregulation of OX-42 and GFAP, which were microglial and astrocytic immunohistochemical activation markers, as well as TNF-α, were consistent with the antinociceptive effects of i.t. Ad-PTEN.

The description of FIG. 7:

FIG. 7 (A)-(C) were immunostaining images, illustrating cells labeled with OX-42 (red) in Spinal cord sections (10 μm) from the 14 days post-surgery from sham-operated plus i.t. vehicle group (FIG. 7 (A)), CCI plus i.t. Ad-GFP group (FIG. 7 (B)), and CCI plus i.t. Ad-PTEN group (FIG. 7 (C)) respectively. Scale bars were 200 μm.

FIG. 7 (D)-(F) were immunostaining images, illustrating cells labeled with GFAP (red) in Spinal cord sections (10 μm) from the 14 days post-surgery from sham-operated plus i.t. vehicle (FIG. 7 (D)), CCI plus i.t. Ad-GFP group (FIG. 7 (E)), and CCI plus i.t. Ad-PTEN group (FIG. 7 (F)) respectively. Scale bars were 200 μm.

FIG. 7 (G)-(I) were immunostaining images, illustrating cells labeled with TNF-α (red) in Spinal cord sections (10 μm) from the 14 days post-surgery from sham-operated plus i.t. vehicle group (FIG. 7 (G)), CCI plus i.t. Ad-GFP group (FIG. 7 (H)), and CCI plus i.t. Ad-PTEN group (FIG. 7 (I)) respectively. Scale bars were 200 μm.

FIG. 7 (J)-(L) were bar graphs of the quantification of OX-42 (FIG. 7 (J)) GFAP (FIG. 7 (K)), and TNF-α (FIG. 7 (L)) immunoreactivity in the affected side of dorsal horn of the lumbar spinal gray matter. Each bar represents the mean±SEM with six rats per group. *P<0.05 compared with sham-operated plus i.t. vehicle group; #P<0.05 compared with CCI plus i.t. Ad-GFP. Ad-PTEN (i.t.) significantly inhibited CCI-induced upregulation of spinal OX-42, GFAP, and TNF-α immunoreactivity.

5. The Effects of Ad-PTEN on Spinal Astrocytic PTEN Signaling in CCI Rats

Further, the effects of i.t. Ad-PTEN on CCI-induced changes in the spinal PTEN pathway were observed. Further, Western blot analysis was used to measure changes in PTEN and phospho-mTOR in the dorsal horn of the lumbar spinal cord from the following six groups of rats: (1) sham-operated plus i.t. vehicle 7 days post injury, (2) CCI plus i.t. Ad-GFP 7 days post injury, (3) CCI plus i.t. Ad-PTEN 7 days post injury, (4) sham-operated plus i.t. vehicle 14 days post injury, (5) CCI plus i.t. Ad-GFP 14 days post injury, and (6) CCI plus i.t. Ad-PTEN 14 days post injury.

The Western blot analysis revealed both a downregulation of PTEN (FIG. 8 (B)) and an upregulation of phospho-mTOR (FIG. 8 (C)) in the spinal cord on days 7 and 14 after CCI surgery, which were both attenuated by i.t. Ad-PTEN.

The description of FIG. 8:

FIG. 8 (A) showed Western blots for PTEN, phospho-mTOR, and β-actin proteins from (1) sham-operated plus i.t. vehicle 7 days post injury, (2) CCI plus i.t. Ad-GFP 7 days post injury, (3) CCI plus i.t. Ad-PTEN 7 days post injury, (4) sham-operated plus i.t. vehicle 14 days post injury, (5) CCI plus i.t. Ad-GFP 14 days post injury, and (6) CCI plus i.t. Ad-PTEN 14 days post injury.

FIG. 8 (B)-(C) showed relative density of the immunoblot of PTEN and phospho-mTOR. Relative band intensities of PTEN and phospho-mTOR were quantified by densitometry and indicated as the percent change relative to that for the sham-operated plus i.t. vehicle 7 days post injury group (100%). Western blotting of β-actin was performed to verify that equivalent amounts of protein were loaded in each lane. Each bar represented the mean±SEM with three rats per group. *P<0.05 compared with sham-operated plus i.t. vehicle 7 days post injury group. #P<0.05 between CCI plus i.t. Ad-PTEN group compared with the same time points in CCI plus i.t. Ad-GFP group. Western blotting revealed that PTEN and phospho-mTOR protein expression were detectable in the sham-operated group, but CCI-induced upregulation of phospho-mTOR and downregulation of PTEN protein on day 7 and day 14 after CCI surgery were both attenuated by i.t. Ad-PTEN.

Compared with the sham-operated plus i.t. vehicle group (FIG. 9 (A)), PTEN immunoreactivity in the CCI plus i.t. Ad-GFP group (FIG. 9 (B)) decreased 14 days post injury.

Compared with the i.t. Ad-GFP group, i.t. Ad-PTEN (FIG. 9 (C)) attenuated CCI-induced downregulation of PTEN 14 days post injury. Compared with the sham-operated plus i.t. vehicle group (FIG. 9 (D)), phospho-mTOR immunoreactivity in the CCI plus i.t. Ad-GFP group (FIG. 9 (E)) increased 14 days post injury. Compared with i.t. Ad-GFP group, i.t. Ad-PTEN (FIG. 9 (F)) attenuated CCI-induced upregulation of phospho-mTOR 14 days post injury. Quantification of the immunoreactivity results further confirmed that i.t. Ad-PTEN significantly attenuated CCI-induced downregulation of PTEN (FIG. 9 (G)) and upregulation of phospho-mTOR (FIG. 9 (H)) 14 days post injury.

The description of FIG. 9:

FIG. 9 (A)-(C) were immunostaining images, illustrating cells labeled with PTEN (red) in Spinal cord sections (10 μm) obtained 14 days post-surgery from sham-operated plus i.t. vehicle group (FIG. 9 (A)), CCI plus i.t. Ad-GFP group (FIG. 9 (B)), and CCI plus i.t. Ad-PTEN group (FIG. 9 (C)). Scale bars were 200 μm.

FIG. 9 (D)-(F) were immunostaining images, illustrating cells labeled with phospho-mTOR (red) in Spinal cord sections (10 μm) obtained 14 days post-surgery from sham-operated plus i.t. vehicle group (FIG. 9 (D)), CCI plus i.t. Ad-GFP group (FIG. 9 (E)), and CCI plus i.t. Ad-PTEN group (FIG. 9 (F)). Scale bars were 200 μm.

FIG. 9 (G)-(H) were bar graphs, showing the quantification of PTEN (FIG. 9 (G)) and phospho-mTOR (FIG. 9 (H)) immunoreactivity in the affected side of dorsal horn of the lumbar spinal gray matter. Each bar represents the mean±SEM with six rats per group.*P<0.05 compared with sham-operated plus i.t. vehicle group; #P<0.05 compared with CCI plus i.t. Ad-GFP.

Ad-PTEN (i.t.) significantly attenuated CCI-induced upregulation of spinal phospho-mTOR immunoreactivity and downregulation of spinal PTEN immunoreactivity.

To examine the inhibitory effects of i.t. injection of Ad-PTEN on CCI-induced upregulation of TNF-α and phospho-mTOR in spinal astrocytes, tissues 14 days post-surgery from sham-operated plus i.t. vehicle (FIG. 10 (A), (D)), CCI plus i.t. Ad-GFP (FIG. 10 (B), (E)), and CCI plus i.t. Ad-PTEN (FIG. 10 (C), (F)) rats were prepared to perform double-immunofluorescent staining.

The confocal doubleimmunostaining results showed that spinal TNF-α (red; FIG. 10 (B)) and phospho-mTOR (red; FIG. 10 (E)) were primarily co-localized with astrocytes in the CCI group, and i.t. Ad-PTEN significantly attenuated CCI-induced upregulation of spinal TNF-α (FIG. 10 (C)) and phosphomTOR (FIG. 10 (F)) immunoreactivity in astrocytes.

The description of FIG. 10:

FIG. 10 (A)-(C) showed confocal double-immunofluorescent staining of TNF-α (red) with GFAP (astrocyte specific marker; green) in the spinal cord sections (10 μm) obtained 14 days post-surgery from sham-operated plus i.t. vehicle group (FIG. 10 (A)), CCI plus i.t. Ad-GFP group (FIG. 10 (B)), and CCI plus i.t. Ad-PTEN group (FIG. 10 (C)). The merged images (yellow; white arrow) indicated co-localization of TNF-α with GFAP immunoreactive cells in the spinal cord. Scale bars were 50 μm.

FIG. 10 (D)-(F) showed confocal double-immunofluorescent staining of phospho-mTOR (red) with GFAP (astrocyte specific marker; green) in the spinal cord sections (10 μm) obtained 14 days post-surgery from sham-operated plus i.t. vehicle group (FIG. 10 D), CCI plus i.t. Ad-GFP group (FIG. 10 (E)), and CCI plus i.t. Ad-PTEN group (FIG. 10 (F)). The merged images (yellow; white arrow) indicated co-localization of phospho-mTOR with GFAP immunoreactive cells in the spinal cord. Scale bars were 50 μm. The confocal results showed that spinal TNF-α and phospho-mTOR were primarily co-localized with astrocytes in the CCI group, whereas i.t. Ad-PTEN significantly attenuated CCI-induced upregulation of spinal TNF-α (FIG. 10 (C)) and phospho-mTOR (FIG. 10 (F)) immunoreactivity in astrocytes.

FIG. 11 (A) was a schematic representation of the possible mechanisms of PTEN involvement in neuropathic pain, in which peripheral nerve injury could downregulate the spinal astrocytic PTEN, leading to the upregulation of phospho-mTOR and TNF-α and resulting in neuroinflammation and nociceptive sensitization. In addition, spinal microglia-astrocyte interactions also promoted nociceptive responses.

FIG. 11 (B) was a schematic representation of the possible mechanisms of PTEN involvement in neuropathic pain, in which through the upregulation of spinal astrocytic PTEN by i.t. Ad-PTEN, peripheral nerve injury-induced upregulation of phospho-mTOR and TNF-α was inhibited, thereby inhibiting neuroinflammation and nociceptive sensitization. The effect of the upregulation of spinal PTEN by i.t. Ad-PTEN on attenuating peripheral nerve injury-induced microglial activation might be through suppressing the astrocyte-microglia interaction by reducing the astrocytic mediator TNF-α.

The content aforementioned is illustrated for fully realizing the present invention. However, the present invention may be implemented in many different forms and should not be construed as limited to the embodiments set forth herein; one skilled in the art may modify and vary the embodiments without departing from the spirit and scope of the present invention, therefore, the embodiments should not be construed as the limitation of the claims.

What is claimed is:

1. A method for treating pain in a subject in need thereof, comprising administering an effective amount of an adenovirus vector to the subject, wherein the adenovirus vector comprises a nucleotide sequence encoding a PTEN protein.

2. The method of claim 1, wherein the pain is an acute pain or a chronic pain.

3. The method of claim 2, wherein the acute pain comprises central nervous system pain and peripheral nervous system pain, visceral pain, headache, migraine headache, Fothergill's neuralgia, atypical facial pain, arthralgia, bone pain, pain caused by cancers or tumor invasion, neuralgia caused by neuropathic pain syndromes, neuropathic pain or pain linked to neuroinflammation.

4. The method of claim 2, wherein the chronic pain comprises central nervous system pain and peripheral nervous system pain, visceral pain, headache, migraine headache, Fothergill's neuralgia, atypical facial pain, arthralgia, bone pain, pain caused by cancers or tumor invasion, neuralgia caused by neuropathic pain syndromes, neuropathic pain or pain linked to neuroinflammation.

5. The method of claim 1, wherein treating pain is to inhibit or to alleviate pain.

6. The method of claim 1, wherein treating pain results from PTEN by attenuating neuroinflammation and/or attenuating upregulation of phospho-mTOR.

7. The method of claim 6, wherein attenuating neuroinflammation is to attenuate microglia and astrocyte activation and/or to attenuate upregulation of TNF-α.

* * * * *